(12) United States Patent
Marshall et al.

(10) Patent No.: US 8,197,485 B2
(45) Date of Patent: Jun. 12, 2012

(54) GRAFT LIGAMENT STRAND TENSIONER

(75) Inventors: Peter Marshall, Bolton, MA (US);
Dennis Hubbard, Lancaster, MA (US)

(73) Assignee: Tyco Healthcare Group LP, Mansfield, MA (US)

(*) Notice: Subject to any disclaimer, the term of this patent is extended or adjusted under 35 U.S.C. 154(b) by 1386 days.

(21) Appl. No.: 11/821,828

(22) Filed: Jun. 26, 2007

(65) Prior Publication Data
US 2008/0033549 A1 Feb. 7, 2008

Related U.S. Application Data

(60) Provisional application No. 60/816,407, filed on Jun. 26, 2006.

(51) Int. Cl.
*A61F 2/46* (2006.01)
(52) U.S. Cl. .......... 606/86 R; 606/88; 606/144
(58) Field of Classification Search .......... 606/186 R, 606/88, 139, 144–148
See application file for complete search history.

(56) References Cited

U.S. PATENT DOCUMENTS

| 4,712,542 A | 12/1987 | Daniel et al. |
| 4,950,271 A | 8/1990 | Lewis |
| 5,037,426 A | 8/1991 | Goble et al. |
| 5,630,820 A | 5/1997 | Todd |
| 6,001,106 A | 12/1999 | Ryan et al. |
| 6,679,889 B1 | 1/2004 | West, Jr. et al. |
| 2003/0176920 A1* | 9/2003 | Sklar et al. ............ 623/13.13 |
| 2004/0024456 A1 | 2/2004 | Brown |

OTHER PUBLICATIONS

International Search Report for corresponding PCT/US07/14784 date of completion is Jun. 24, 2008 (1 page).
European Search Report for corresponding EP07809890 date of mailing is Feb. 10, 2012 (3 pgs.).

* cited by examiner

*Primary Examiner* — Andrew Yang

(57) ABSTRACT

A graft ligament strand tensioner is provided. The tensioner includes a body, a pair of suture rails connected to the body and a handle pivotally connected to the body. Each suture rail comprises a grooved outer channel for receiving a suture loop and a central mandrel for receiving a suture loop. The handle is pivotally connected to the body such that the handle can be pivoted relative to a longitudinal axis of the body only when the handle is under tension.

4 Claims, 34 Drawing Sheets

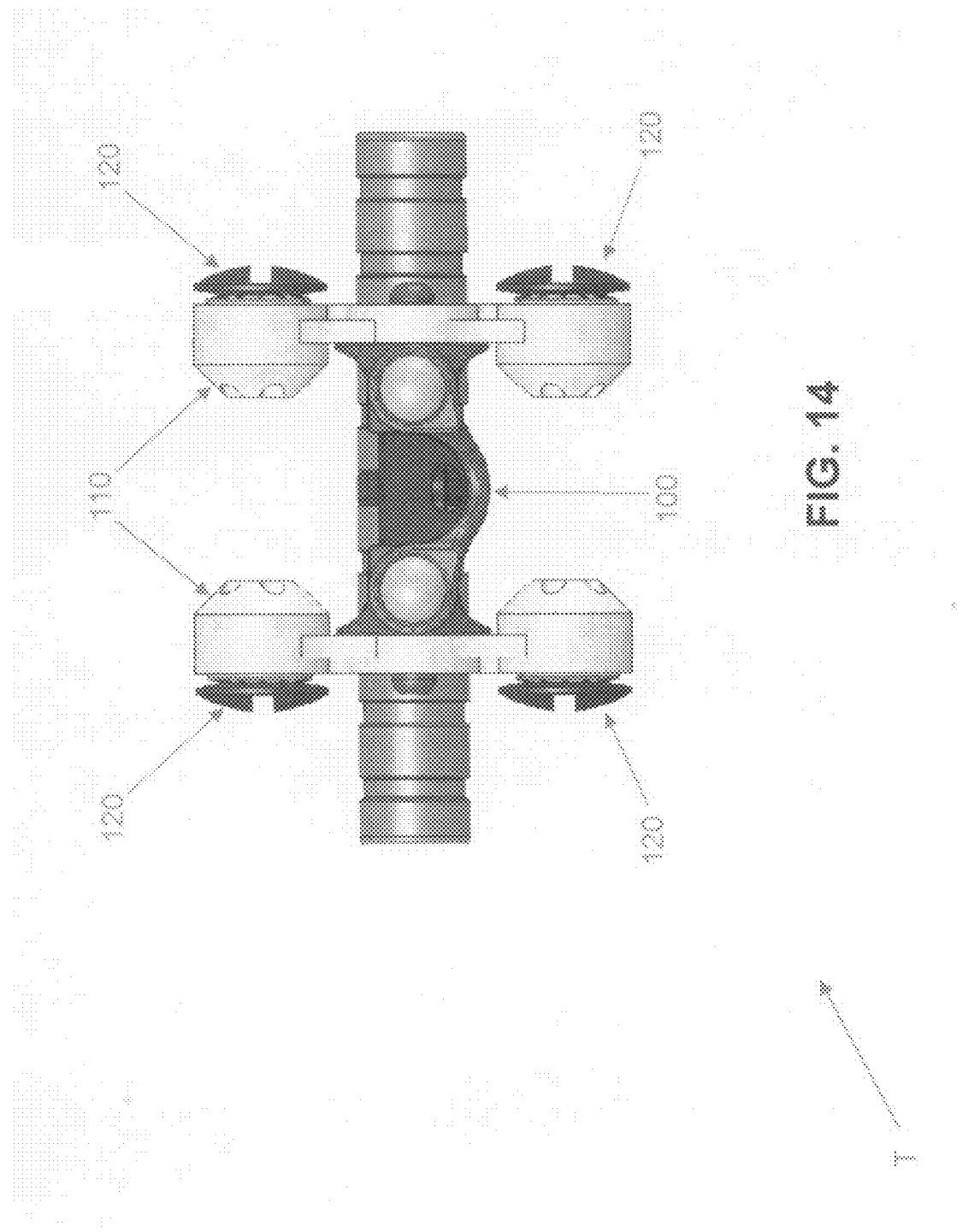

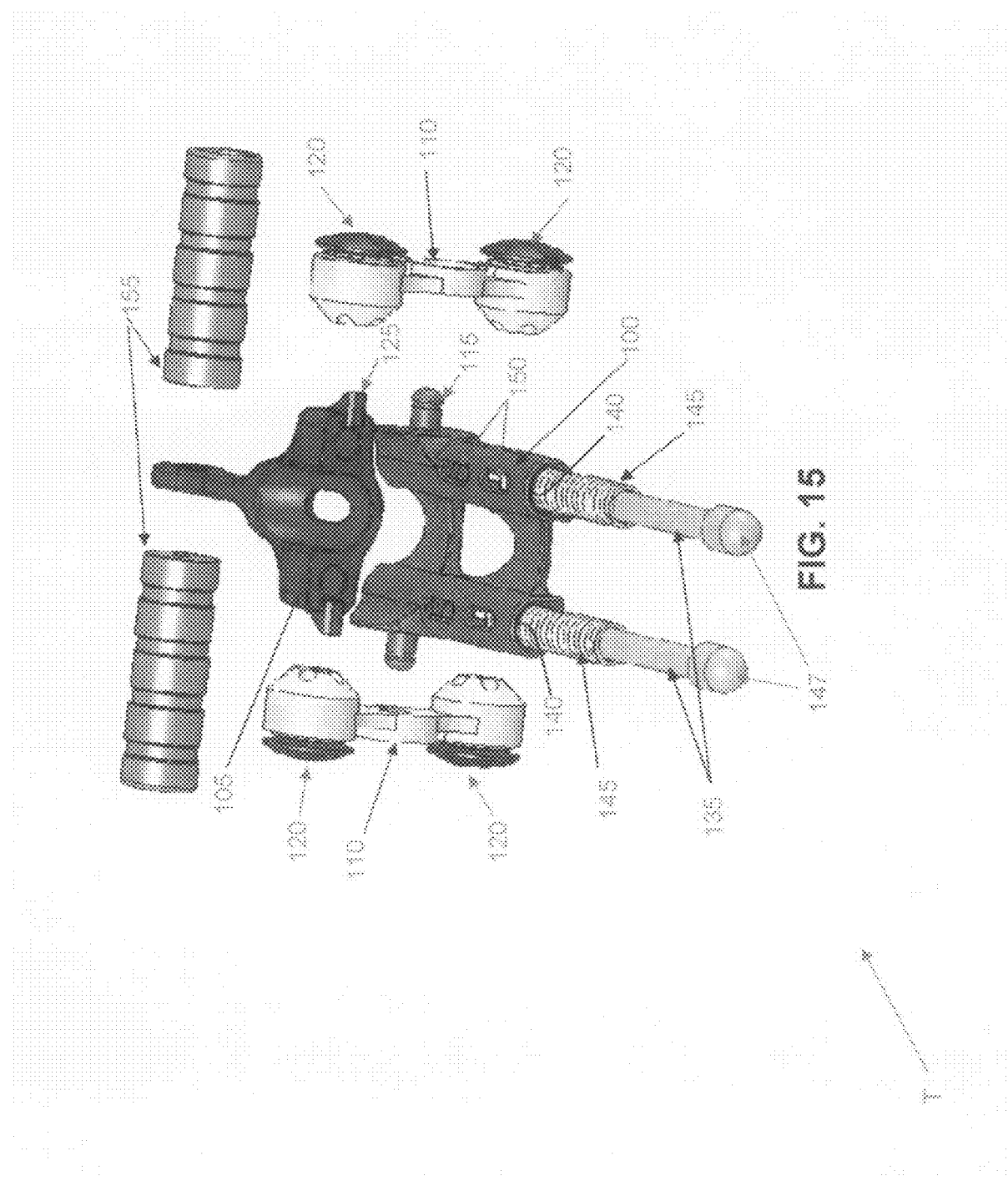

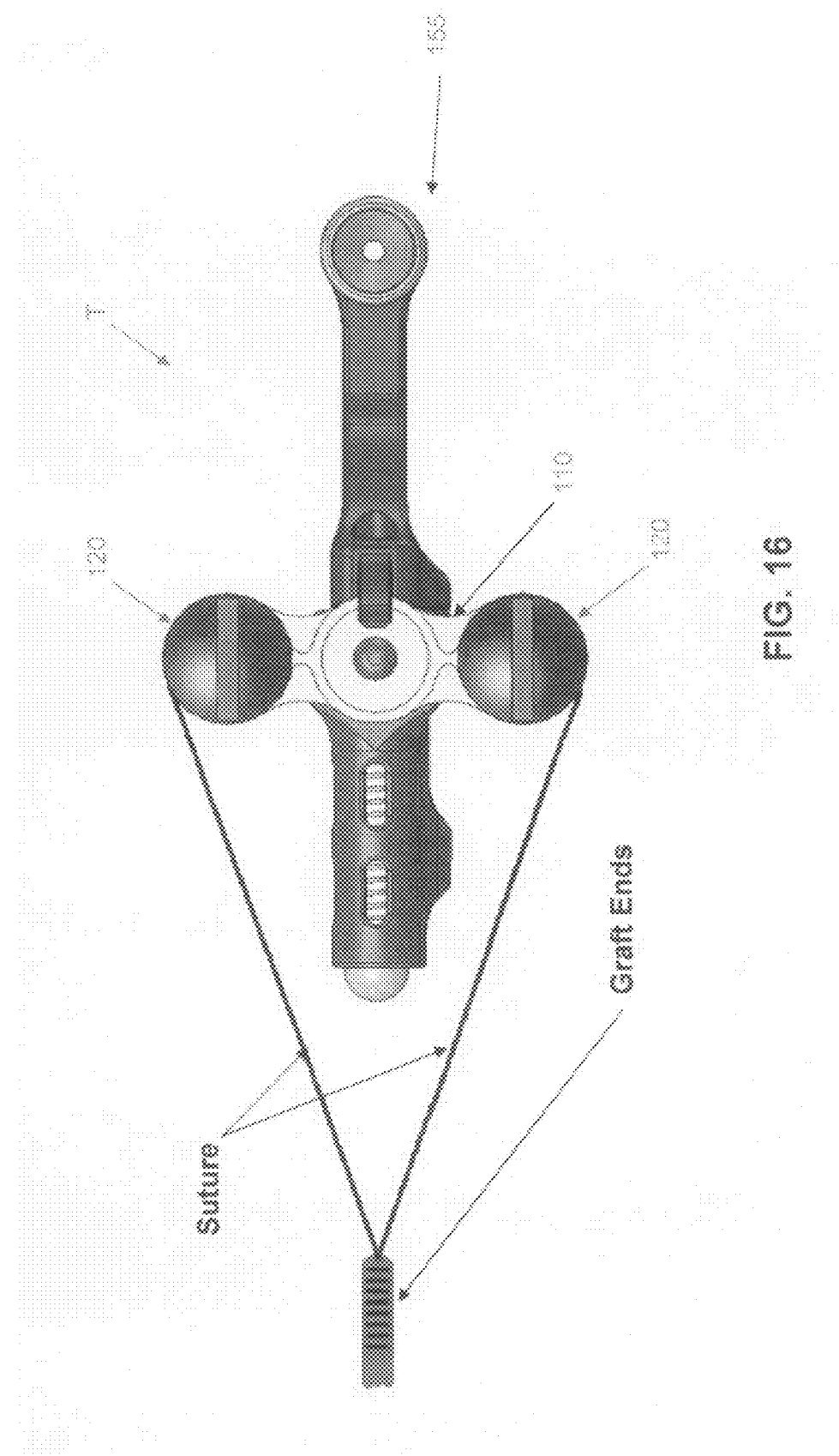

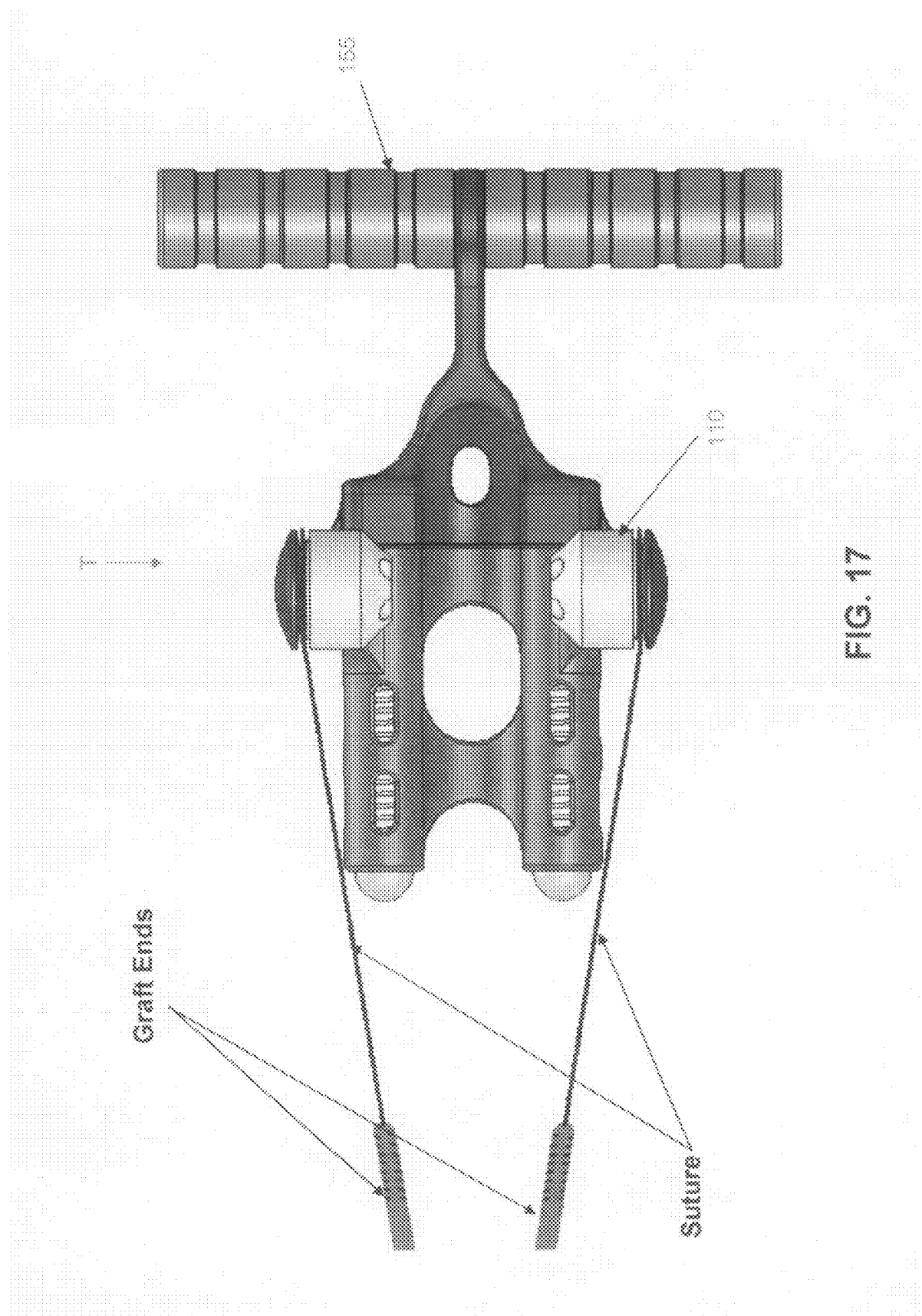

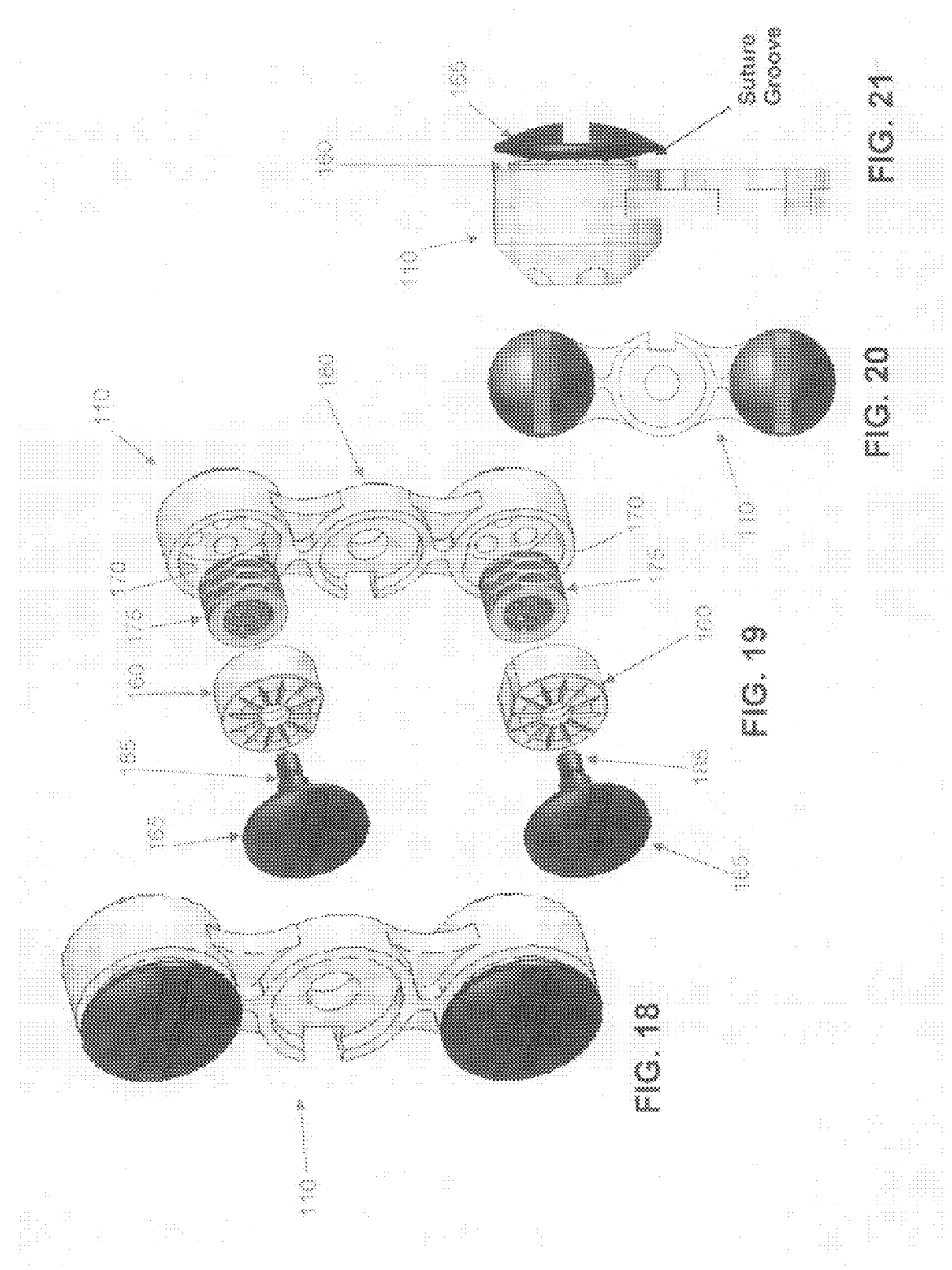

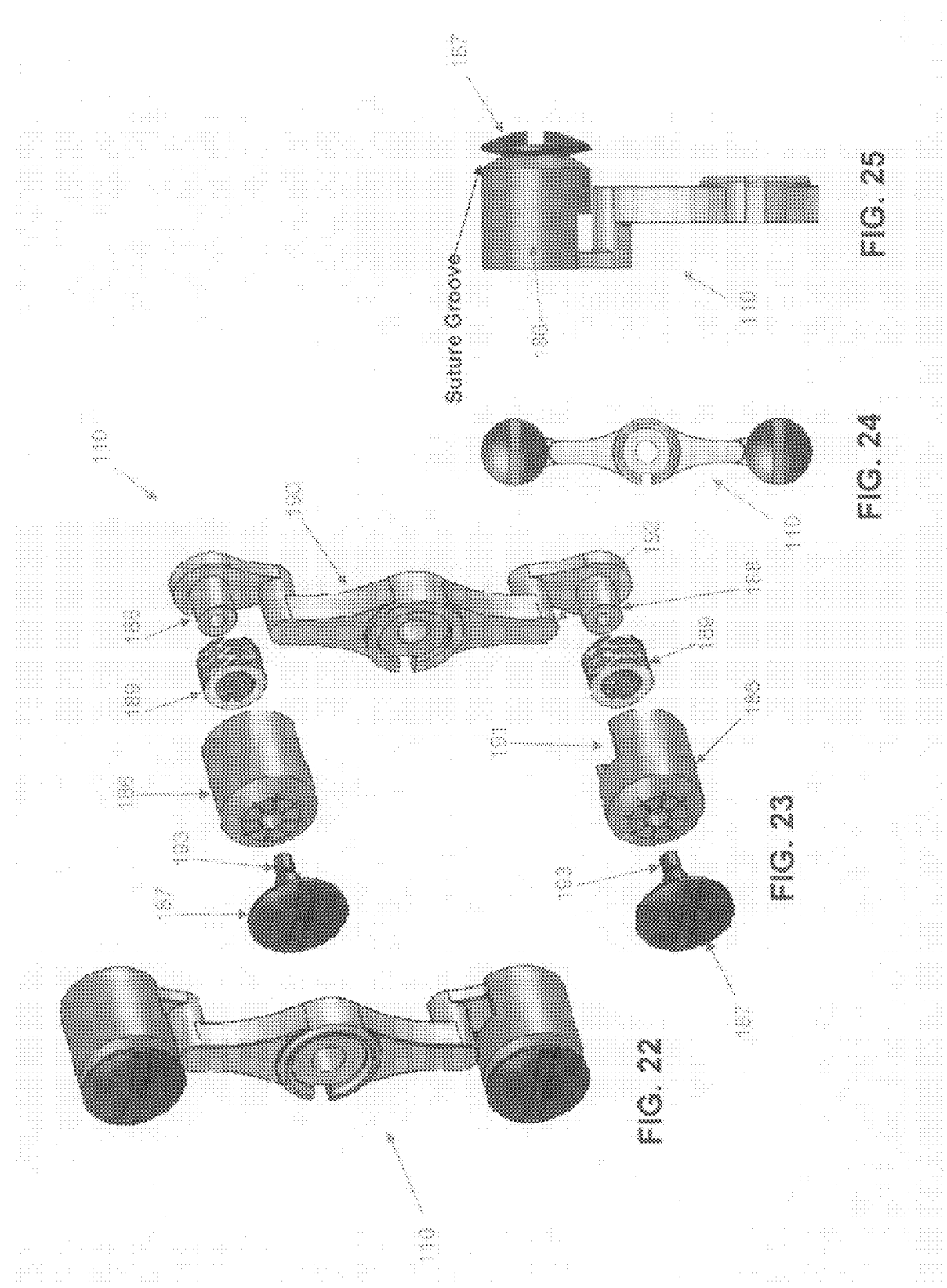

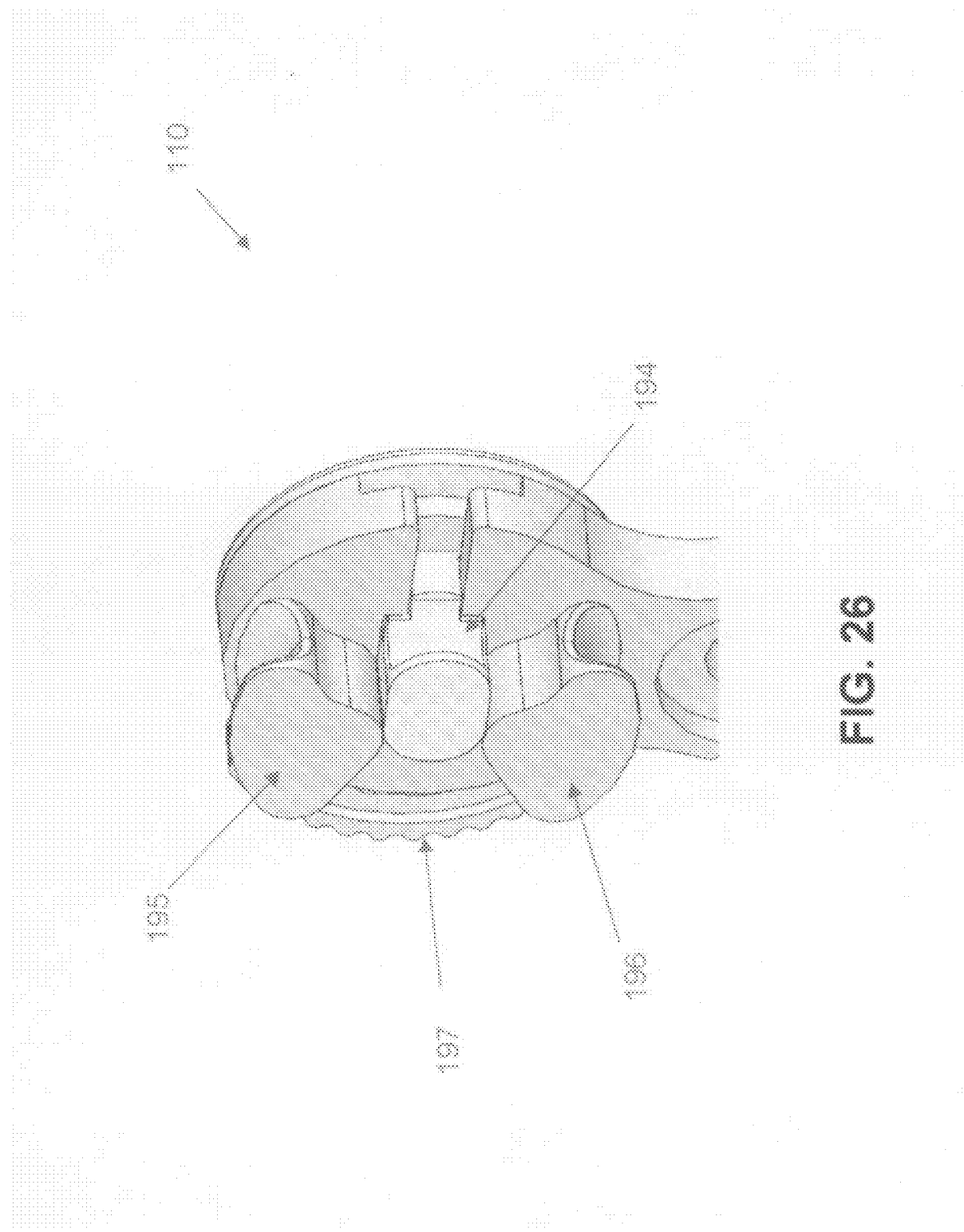

GRAFT LIGAMENT STRAND TENSIONER

REFERENCE TO PENDING PRIOR PATENT APPLICATION

This patent application claims benefit of pending prior U.S. Provisional Patent Application Ser. No. 60/816,407, filed Jun. 26, 2006 by Peter Marshall et al. for GRAFT LIGAMENT STRAND TENSIONER, which patent application is hereby incorporated herein by reference.

FIELD OF THE INVENTION

This invention relates to medical devices in general, and more particularly to devices for simultaneously positioning and tensioning, to a selected tension, a plurality of graft ligament strands.

BACKGROUND OF THE INVENTION

It is known in the art to use four graft ligament strands, such as two gracilis strands (e.g., a gracilis tendon doubled over) and two semitendinosus strands (e.g., a semitendinosus tendon doubled over), in the reconstruction of an anterior cruciate ligament (ACL). It is further known in the art to use other numbers of graft ligament strands, such as one, two or three strands, in an ACL reconstruction. It is also known in the art to use other anatomical materials, such as a patellar tendon, a quadriceps tendon, a tibialis tendon, etc., for an ACL reconstruction.

It is also known in the art to reconstruct other (i.e., non-ACL) ligaments using similar techniques. By way of example but not limitation, it is known in the art to reconstruct a posterior cruciate ligament (PCL) using similar techniques.

When using more than one graft ligament strand for a ligament reconstruction, it is generally preferred that the various ligament strands be equally tensioned, since this generally provides the best biomechanical results. The tension on each graft ligament strand may be applied by hand, one ligament at a time, but this approach is relatively time-consuming and makes it difficult to reliably tension each ligament strand to an equal, desired tension. Furthermore, this approach is generally impractical where the several graft ligament strands are to be secured to the host bone using a single fastener or anchor.

It is also possible to tension the graft ligament strands by hanging weights from each graft ligament strand. While this approach provides a known, equal tension on each graft ligament strand, it is generally fairly time-consuming to attach the weights to the various graft ligament strands. Furthermore, it can be awkward for the surgeon to work around the weights, which are hanging down from the free ends of the graft ligament strands, particularly at the point in the procedure when the surgeon is securing the graft ligament strands to the host bone (e.g., to the tibia, in the case of an ACL reconstruction).

Additionally, where a plurality of graft ligament strands are used in a graft ligament reconstruction and the plurality of graft ligament strands are being secured to the host bone using a single fastener or anchor, it is generally advantageous to be able to manipulate all of the graft ligament strands simultaneously, with an equal tension being applied to each graft ligament strand. However, applying tension equally to each of the several graft ligament strands can be complicated in situations where the graft ligament strands are positioned and tensioned using sutures extending from the strands, since the sutures are often not the same length.

Accordingly, there is a need for a new and improved graft ligament strand tensioner which may be used to simultaneously position and tension, to a desired tension, a plurality of graft ligament strands.

SUMMARY OF THE INVENTION

These and other objects of the present invention are addressed by the provision and use of the novel graft ligament strand tensioner which is hereinafter disclosed.

In one form of the invention, there is provided a graft ligament strand tensioner comprising:
a body; and
a pair of suture rails connected to the body, wherein each suture rail comprises a grooved outer channel for receiving a suture loop and a central mandrel for receiving a suture loop, wherein the separation of a suture loop received by the grooved outer channel is larger than the separation of a suture loop received by the central mandrel.

In another form of the present invention, there is provided a graft ligament strand tensioner comprising:
a body; and
a plurality of cleats connected to the body, wherein each of the cleats is configured to releasably secure a length of suture.

In another form of the present invention, there is provided a graft ligament strand tensioner comprising:
a body;
at least two suture-engaging elements for releasably engaging a pair of sutures, the at least two suture-engaging elements being connected to the body, in spaced-apart fashion, symmetrically about a center axis of the body; and
a handle pivotally connected to the body, such that the handle can be laterally positioned relative to the longitudinal axis of the body.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIGS. 12-17 show a second preferred embodiment of the novel graft ligament strand tensioner of the present invention;

FIGS. 18-29 show various cleat assemblies which may be used with the novel graft ligament strand tensioner shown in FIGS. 12-17;

DETAILED DESCRIPTION OF THE PREFERRED EMBODIMENTS

First Preferred Embodiment of the Novel Tensioner

Figure 1:
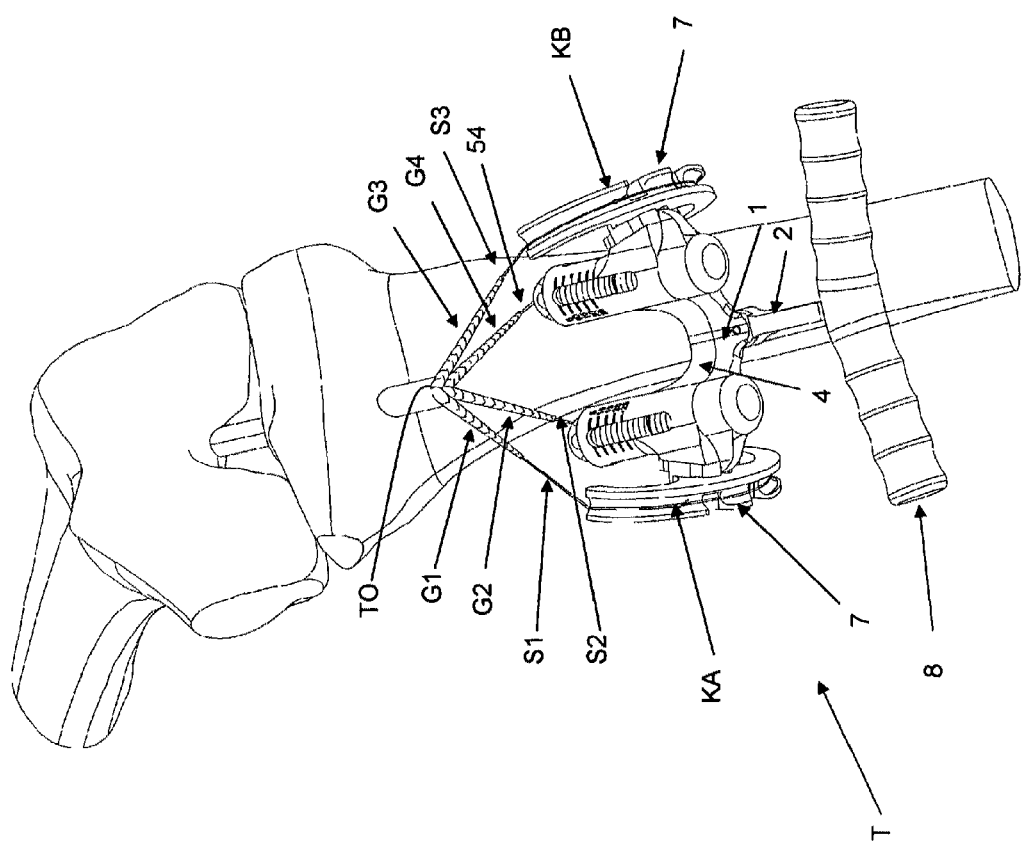
FIGS. 1-11 show a first preferred embodiment of the novel graft ligament strand tensioner of the present invention.
Figure 2:
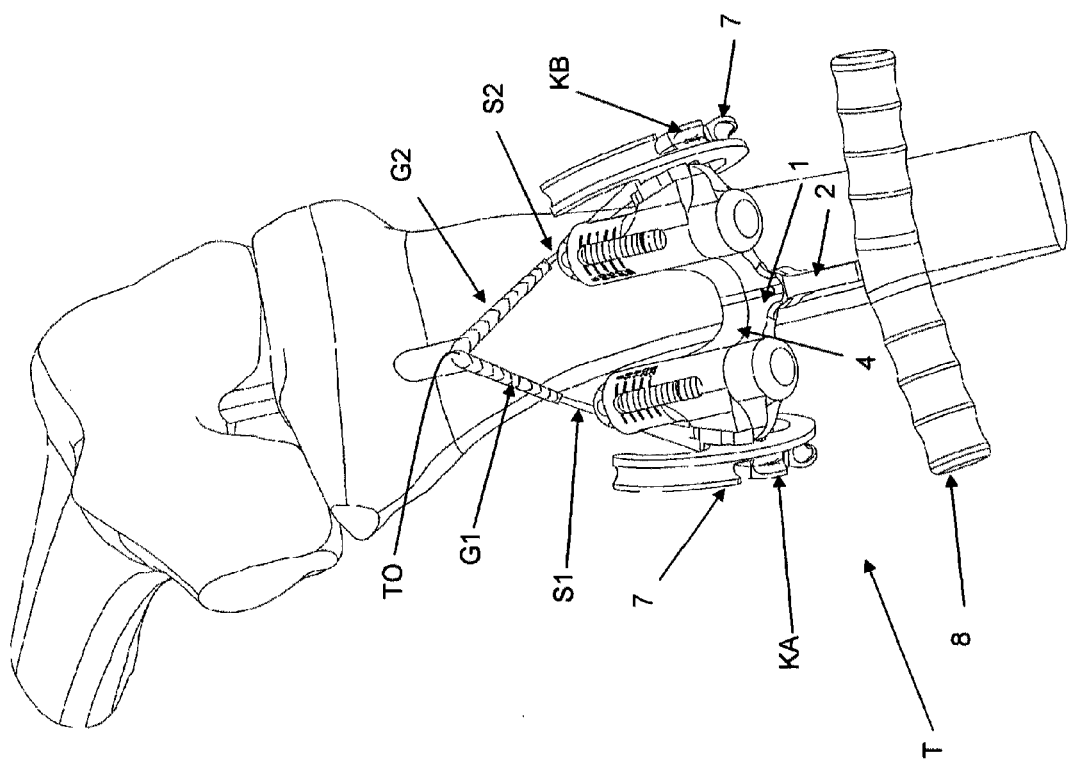
Figure 3:
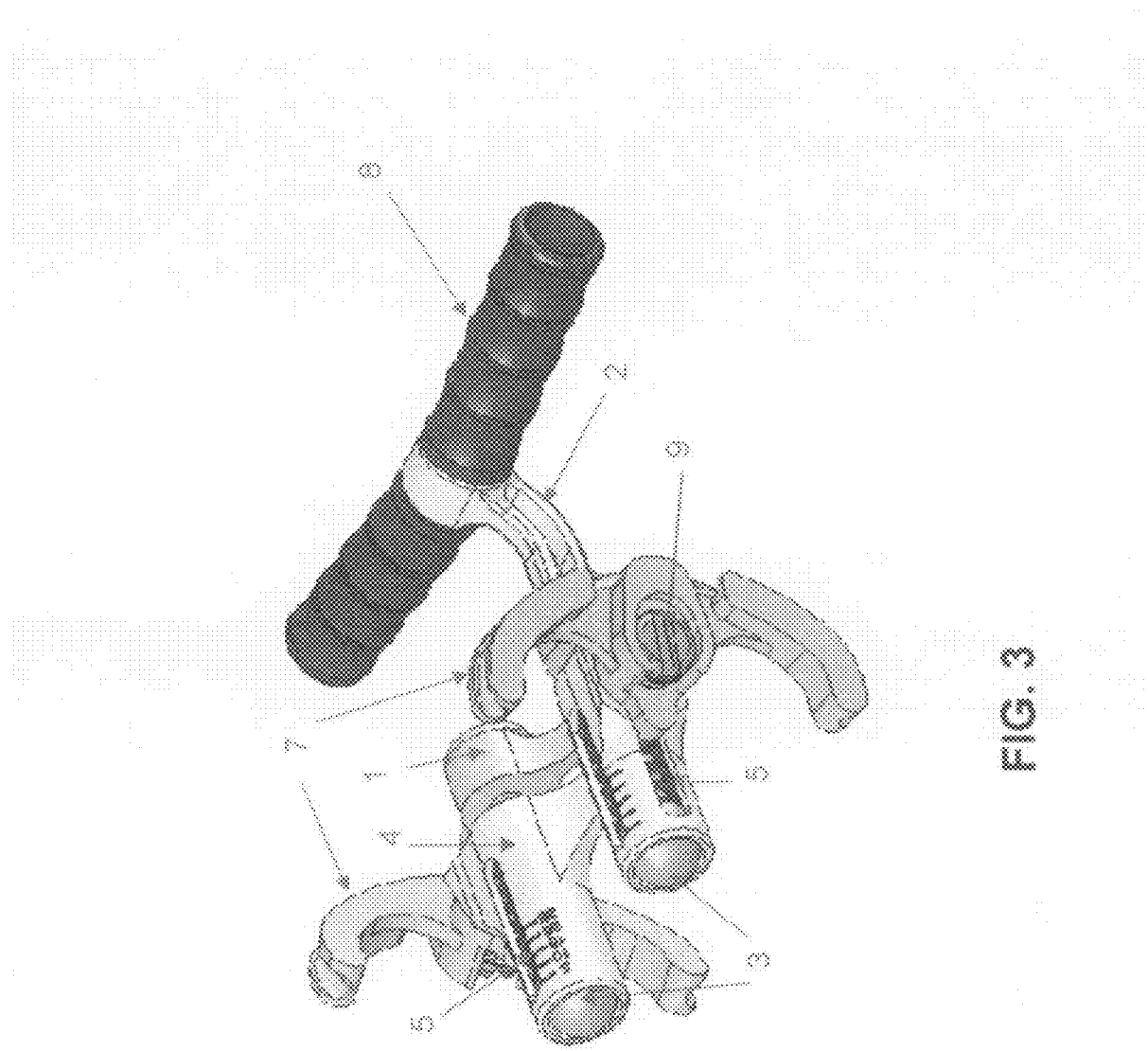
Figure 4:
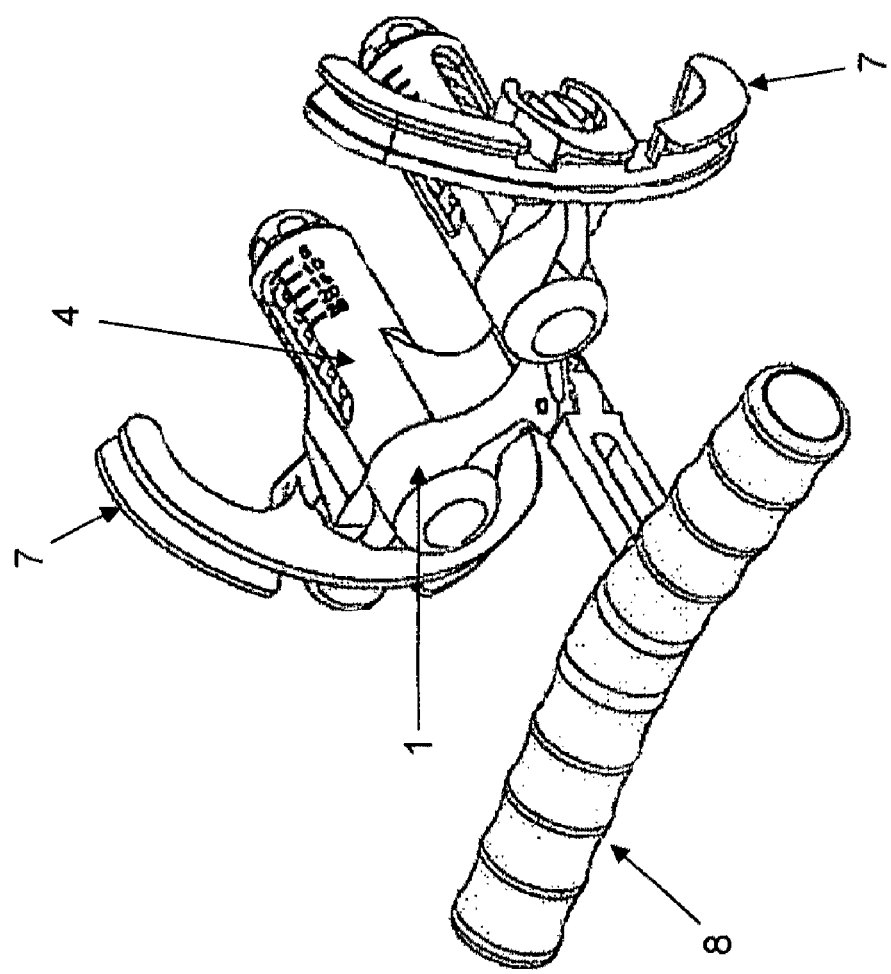

Looking first at FIGS. 1-11, there is shown a first preferred embodiment of the novel graft ligament strand tensioner. More particularly, the novel graft ligament strand tensioner T generally comprises a handle body 1 (FIG. 6), a handle beam 2, a pair of slide rails 3 (FIG. 11), a slide body 4, a pair of compression springs 5 (FIG. 11), a handle pivot pin 6, a pair of suture rails 7, a pair of handle grips 8, a pair of retaining pins 9 (FIG. 3), and a pair of retaining pin springs 10 (FIG. 11), all of which are assembled together in the manner shown in the drawings, and as hereinafter discussed, so as to form the complete tensioner T. Tensioner T may be used to position and tension a plurality (e.g., four or two) graft ligament strands in the course of effecting a ligament (e.g., an ACL) reconstruction. By way of example but not limitation, FIG. 1 shows tensioner T being used in a four-strand ligament reconstruction, and FIG. 2 shows tensioner T being used in a two-strand ligament reconstruction.

Figure 7:
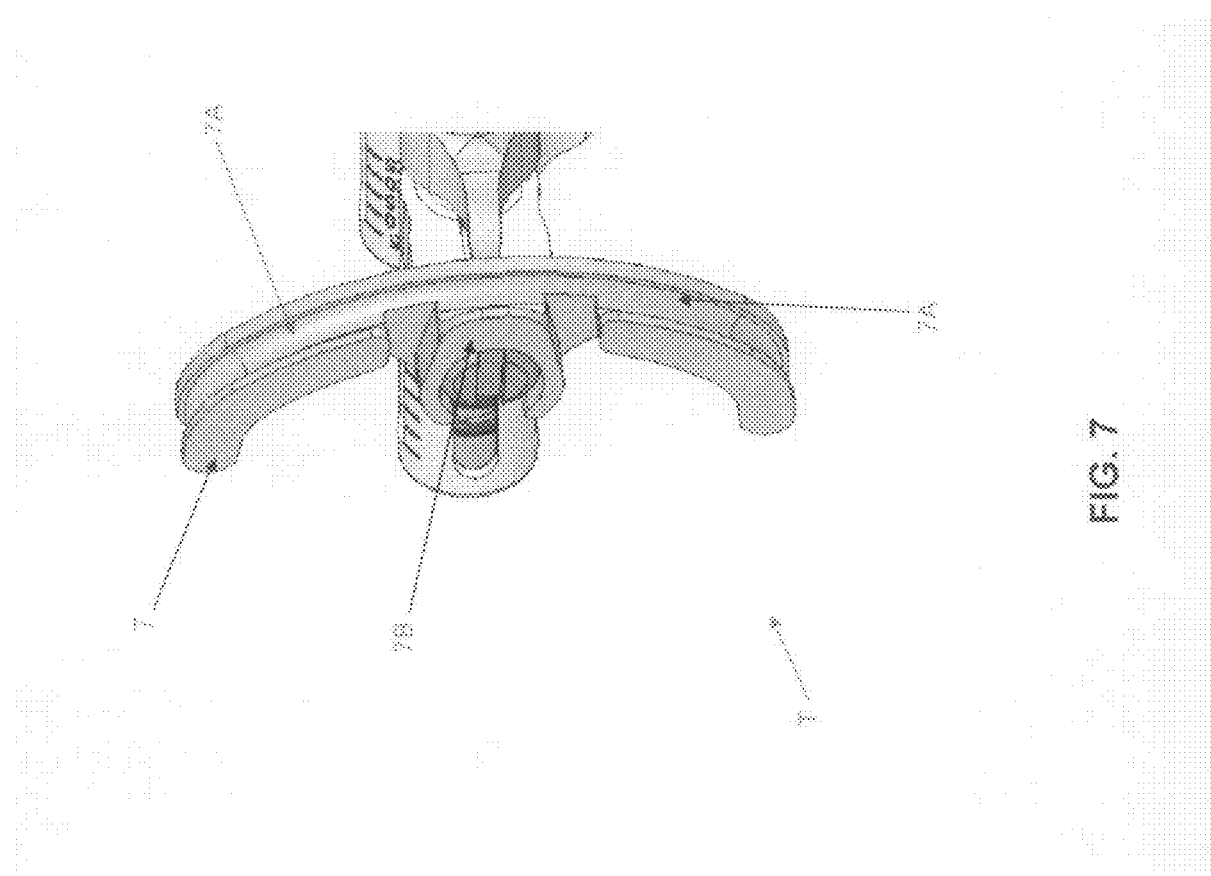
Figure 8:
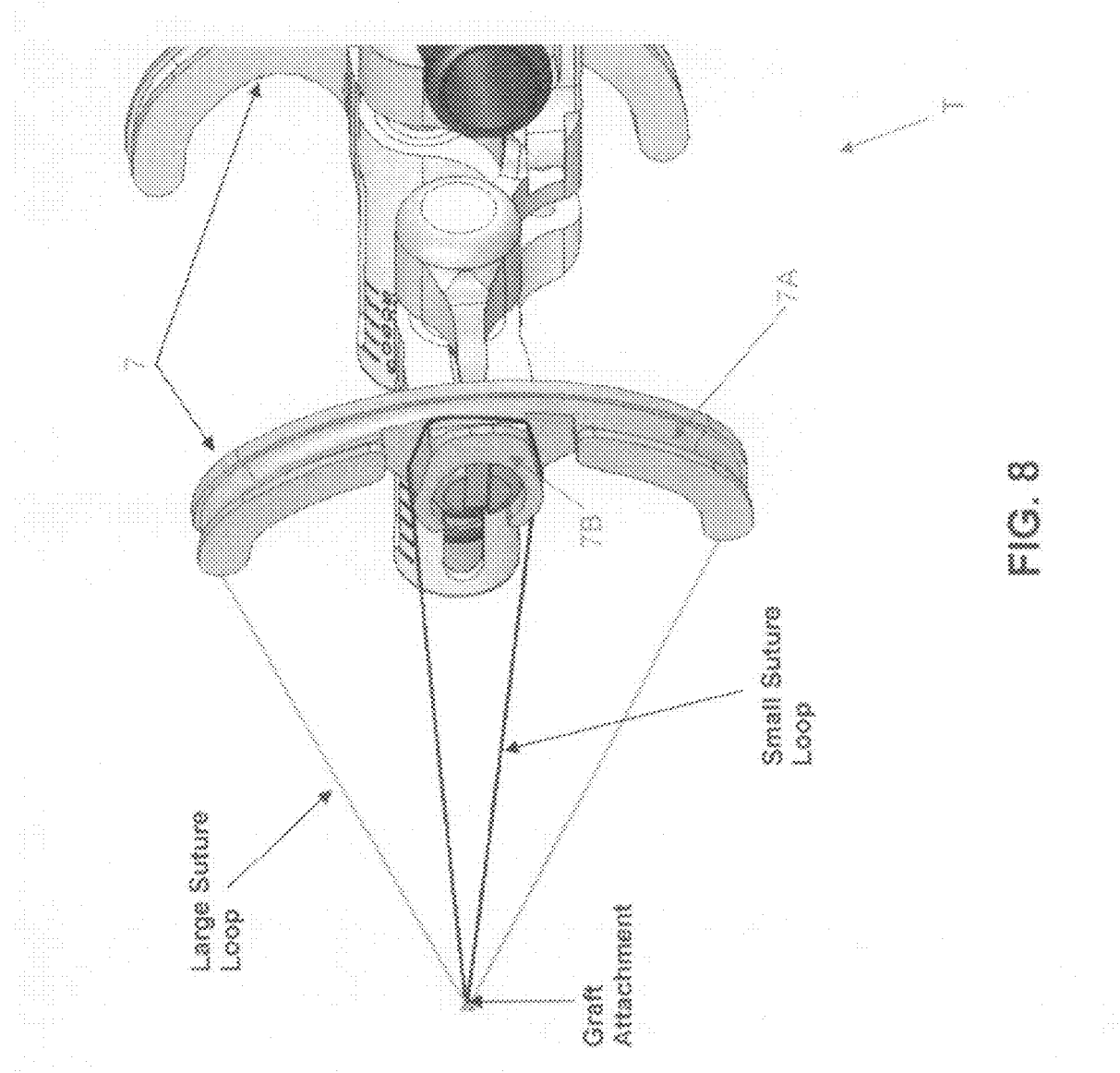
Figure 9:
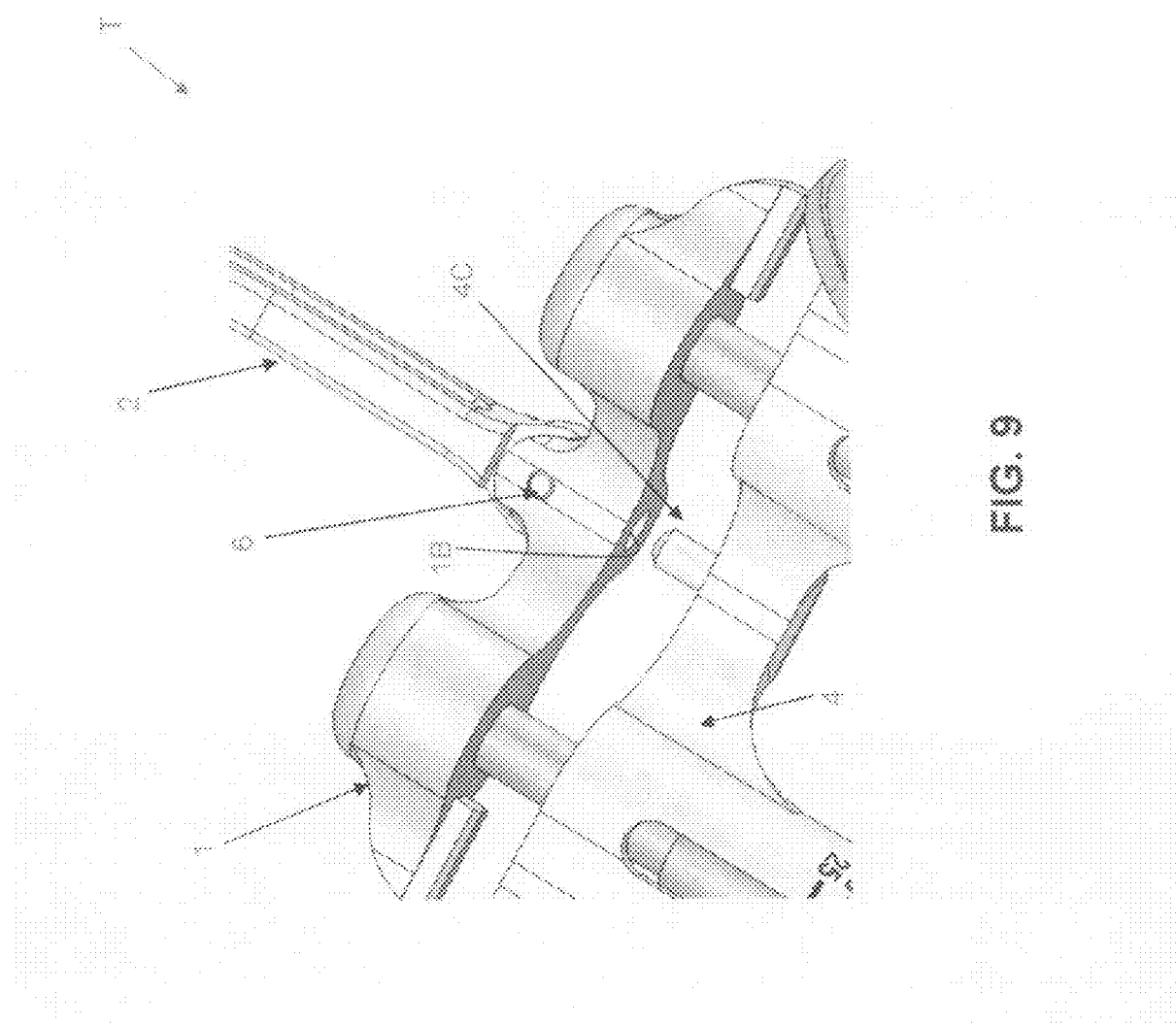
Figure 11:
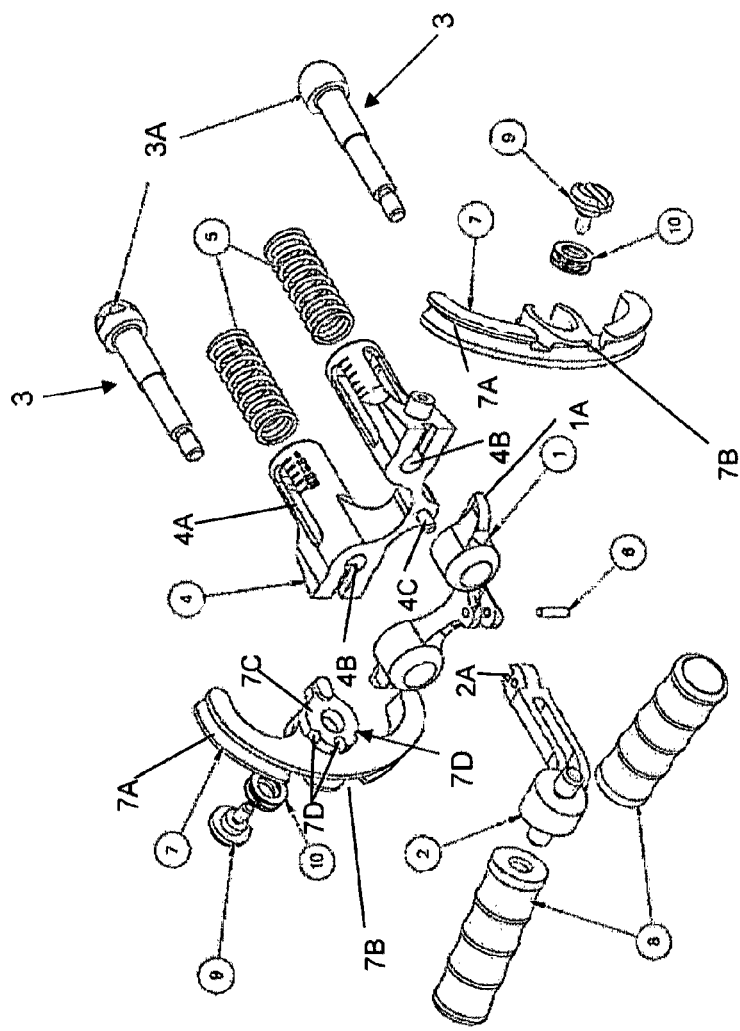
Figure 12:
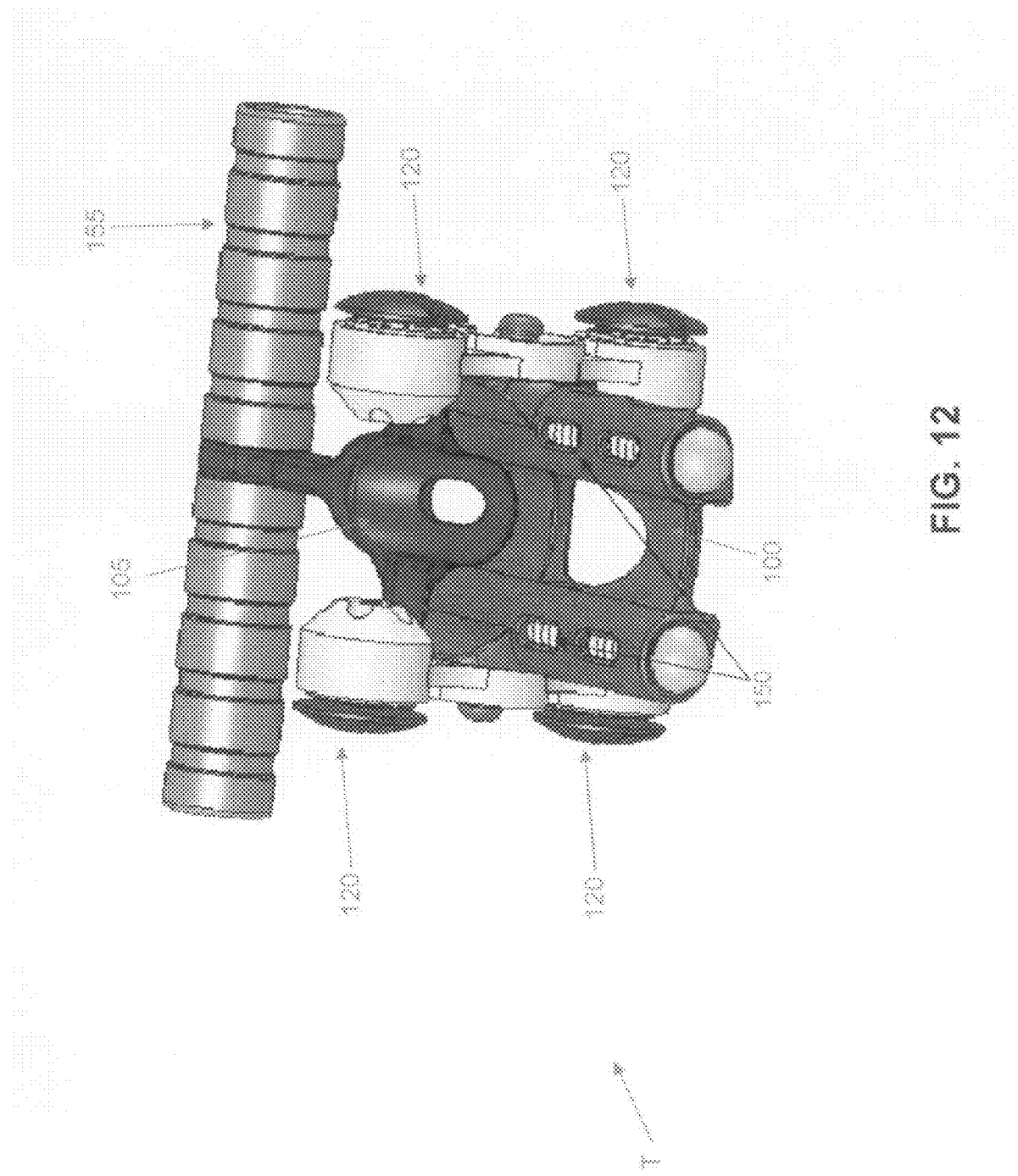

More particularly, tensioner T comprises a slide body 4 (FIG. 11) having two suture rails 7 attached thereto. Suture rails 7 are pinned to the sides of slide body 4 with retaining pin springs 10 and retaining pins 9. Each suture rail 7 preferably has two suture guides, a grooved outer channel 7A and a central mandrel 7B (FIGS. 7, 8 and 11). The grooved outer channels 7A are preferably used as the suture guides during a four-strand graft reconstruction (FIG. 1), and the central mandrels 7B are preferably used as the suture guides during a two-strand graft reconstruction (FIG. 2).

More particularly, during a four-strand graft reconstruction (e.g., an autograft procedure), it is generally desirable for the surgeon to keep each of the graft strands physically and visually separated from one another. The arched shape of the suture rails 7, and hence the grooved outer channels 7A, are designed so as to provide optimal vertical separation of the graft strands, and hence provide optimal visibility to the surgeon and optimal positioning of the graft strands, during reconstruction. During a two-strand graft reconstruction (e.g., an allograft procedure), there is no need to vertically separate two adjacent ligament strands, and any application of vertical separation forces to a single graft strand creates a risk that the single graft strand will tear during the procedure. This is due to the nature of the graft strand material itself and to any vertical separation forces applied to the single graft ligament strand. By looping the two sutures of a single graft ligament strand around the smaller central mandrel 7B, rather than around the larger grooved outer channels 7A, the risk of tearing the graft during a two-strand reconstruction procedure is significantly reduced. Thus, by providing two suture guide options (e.g., the larger outer groove channels 7A and the smaller central mandrels 7B), the surgeon is free to choose the suture position which will best suit the particular graft reconstruction being effected.

In addition to the foregoing, suture rails 7 are designed to work with sutures of different sizes and lengths. More specifically, the arched designs of outer groove channels 7A and inner central mandrels 7B permit the sutures to be tied in loops so as to eliminate the need for surgeons to precisely prepare each suture with identical lengths and positions in order to apply symmetric, simultaneous tension to the graft.

Figure 10:
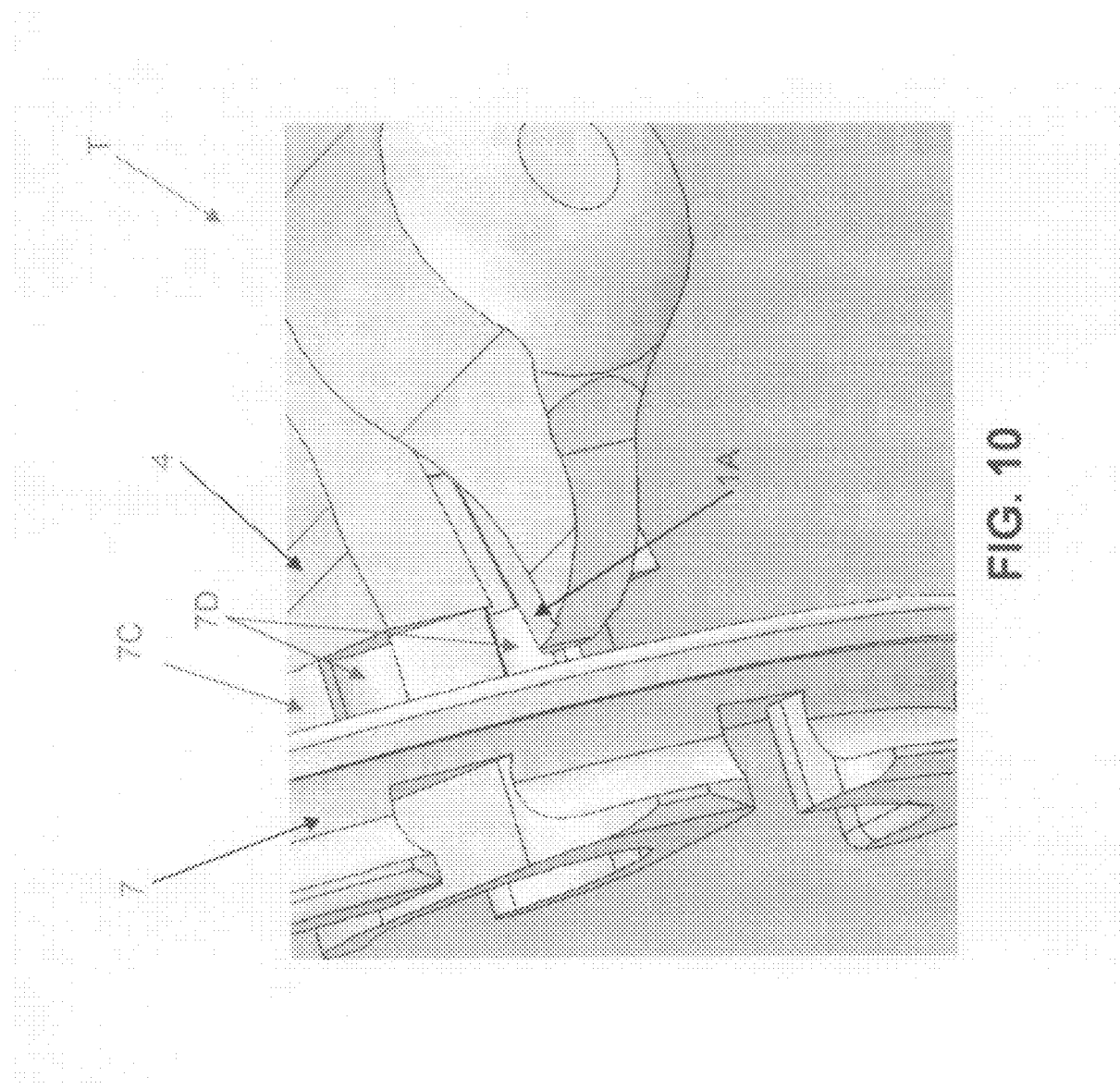

Suture rails 7 have inner hubs 7C (FIG. 11) with three lock grooves 7D (FIGS. 10 and 11). The lock grooves 7D allow the suture rails 7 to lock in particular rotational orientations relative to slide body 4, using locking fins 1A (FIGS. 10 and 11) of handle body 1, thereby allowing for easier cleaning and storage of the assembled tensioner.

Figure 5:
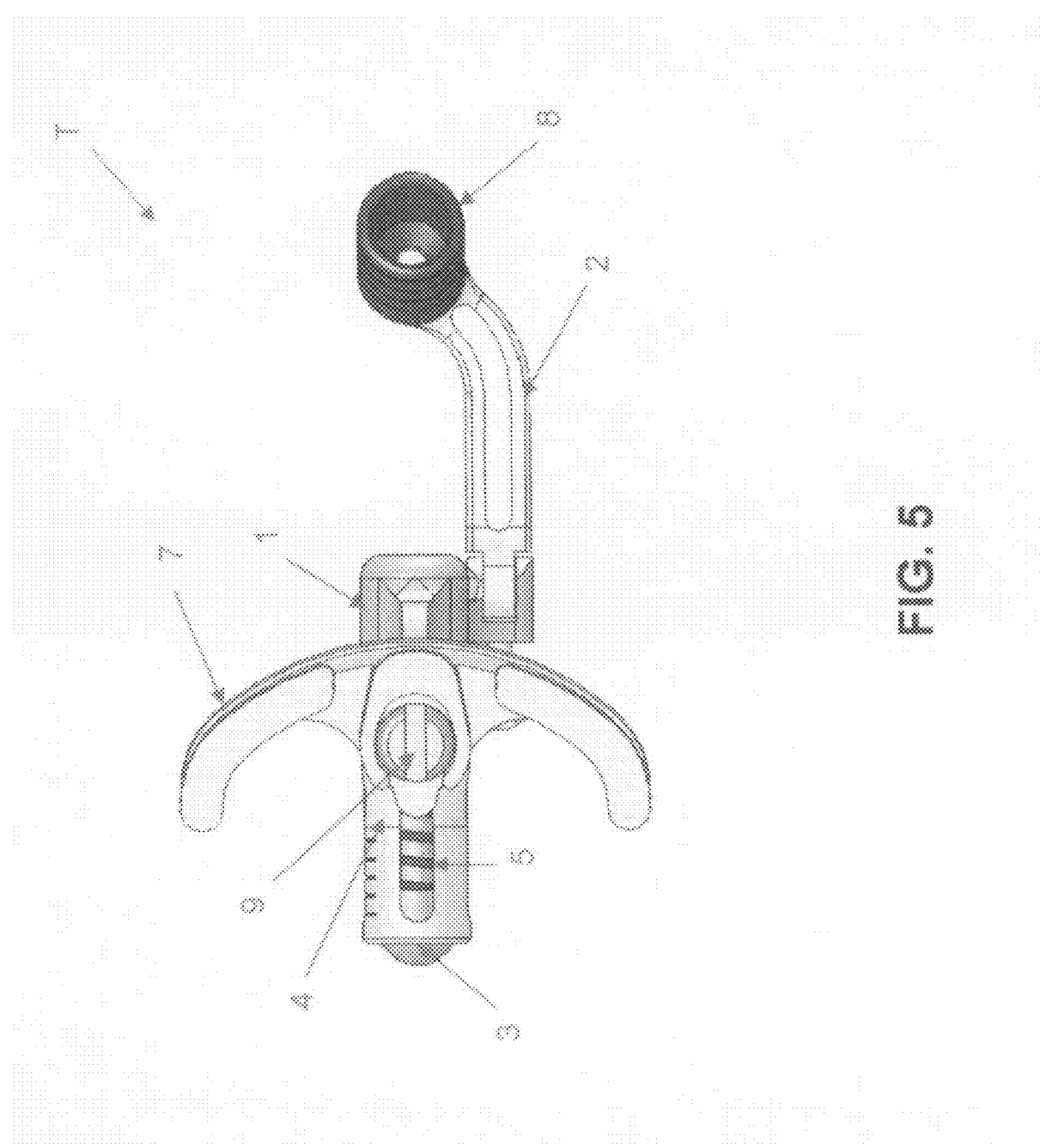
Figure 6:
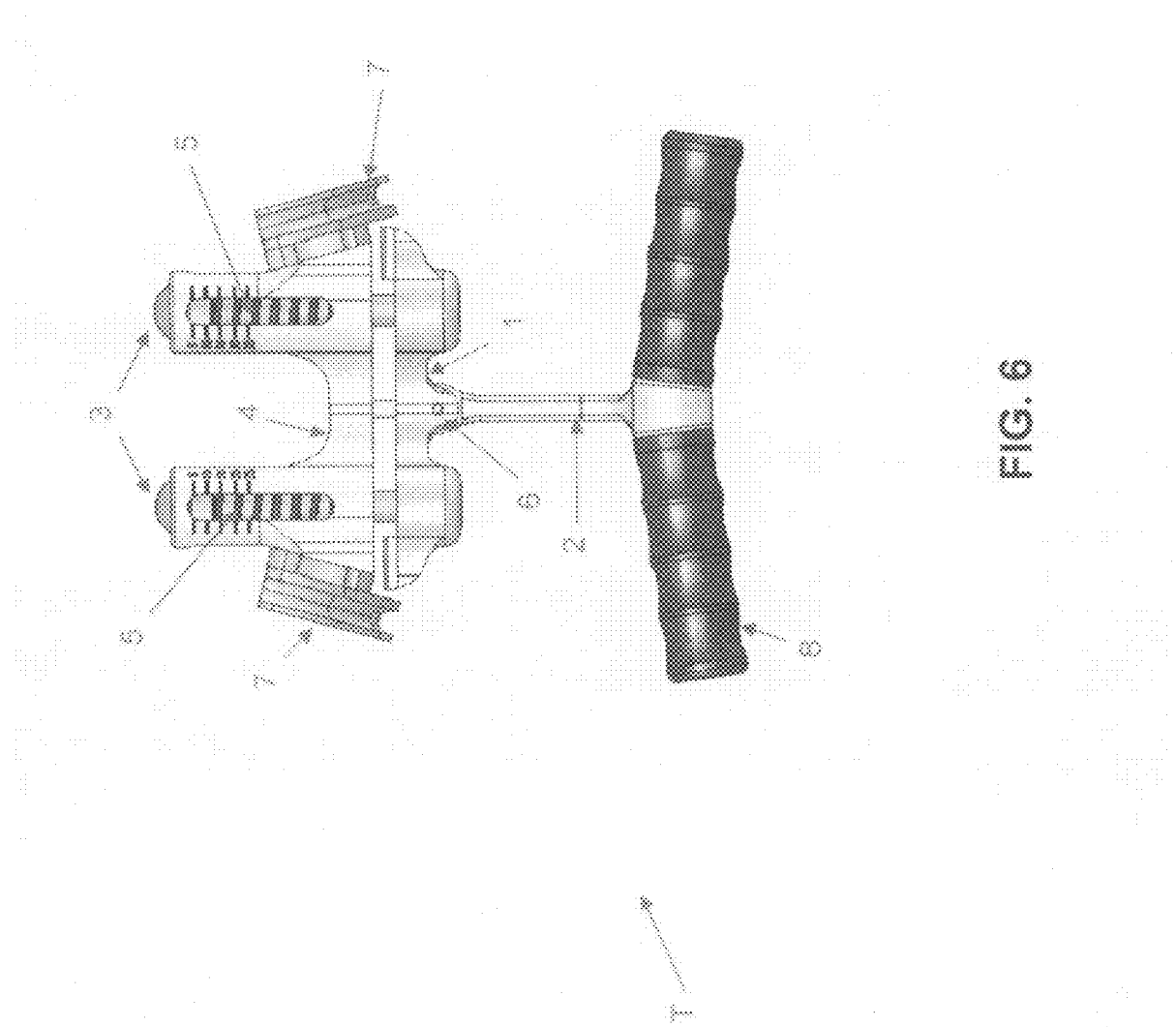

Handle body 1 is spring biased against slide body 4 (FIG. 5). More particularly, handle body 1 is connected to slide body 4 by slide rails 3 (FIG. 11) which (i) extend through bores 4A formed within slide body 4, (ii) extend through lumens 4B formed in slide body 4, and (iii) mount in handle body 1. Compression springs 5 are captured between the enlarged heads 3A of slide rails 3 and the annular shoulders formed at the interior bases of bores 4A. Locking fins 1A are located on the distal end of handle body 1 for selectively engaging lock grooves 7D (FIG. 10) on suture rails 7 as noted above.

Bores 4A are partially open so that the surgeon may view both the compression springs 5 and slide rails 3 within the interior of slide body 4 (FIG. 5). Markings (FIGS. 5 and 6) alongside slide body 4 indicate the amount of tension applied to the graft ligament strands so as to provide the surgeon with a visual gauge of the tension being applied during the ligament reconstruction procedure.

Handle 8 (FIG. 1) is connected to handle body 1 by a handle beam 2. Handle beam 2 is in turn attached to handle body 1 by a handle pivot pin 6 (FIG. 11). Furthermore, slide body 4 has a finger 4C (FIGS. 9 and 11) which projects proximally from slide body 4, extending through an opening 1B in handle body 1 and is selectively received in a locking groove 2A (FIG. 11) within handle beam 2. In view of the foregoing construction, (i) when tensioner T is not under load, handle 8 is locked in position by virtue of finger 4C seating in locking groove 2A; and (ii) when tensioner T is under load, finger 4C is no longer seated in locking groove 2A (FIG. 9) and handle 8 is free to rotate laterally about pivot pin 6, whereby to minimize off-axis loading when tensioning the graft ligament strands. Handle 8 has a contoured grip (FIG. 3) and is configured so as to enable one-handed use by the surgeon during the ligament reconstruction procedure.

The graft ligament tensioner T of the present invention will now be discussed in the context of its use in a four-strand ACL reconstruction (FIG. 1), however, it should be appreciated that tensioner T may also be used in a two-strand reconstruction (FIG. 2), as well as in other multiple-strand graft reconstructions.

In use, and looking now at FIG. 1, sutures S1 and S2, extending from gracilis graft ligament strands G1 and G2, are tied together at a knot KA at a selected distance from tibial tunnel opening TO. Then sutures S1 and S2 are looped around suture rail 7 in grooved outer channel 7A. Similarly, sutures S3 and S4, extending from semitendinosus graft ligament strands G3 and G4, are tied together at knot KB and looped around the other suture rail 7 in grooved outer channel 7A. Then the surgeon, holding tensioner T by handle 8, pulls proximally away from the patient. As tensioner T is pulled back, handle body 1 is pulled away from slide body 4, against the bias of compression springs 5, and the graft ligaments are tensioned. As mentioned above, the degree of tension being applied to the graft ligaments strands can be measured by observing the degree of compression of springs 5 vis-à-vis the visual indicia (FIGS. 5 and 6) marked on slide body 4. This construction allows the surgeon to accurately determine when the selected degree of tension has been has been applied to the graft ligament strands during the reconstruction procedure. As handle body 1 is pulled away from slide body 4, handle beam 2 moves away from finger 4C formed on slide body 4 (FIG. 9), freeing handle 8 for appropriate lateral positioning by the surgeon so as to equalize the tension on each of the ligament strands. Once the graft ligaments have been equally tensioned, the graft ligament strands are secured to the bone by any of the several fixation techniques well known to those skilled in the art.

In a reconstruction procedure where two ligament strands are to be used (FIG. 2), the aforementioned procedure is preferably implemented with two sutures strands S1 and S2 looped around the two center mandrels 7B (FIG. 8), rather than the outer grooved channels 7A of the suture rails 7.

Second Preferred Embodiment of the Novel Tensioner

Figure 13:
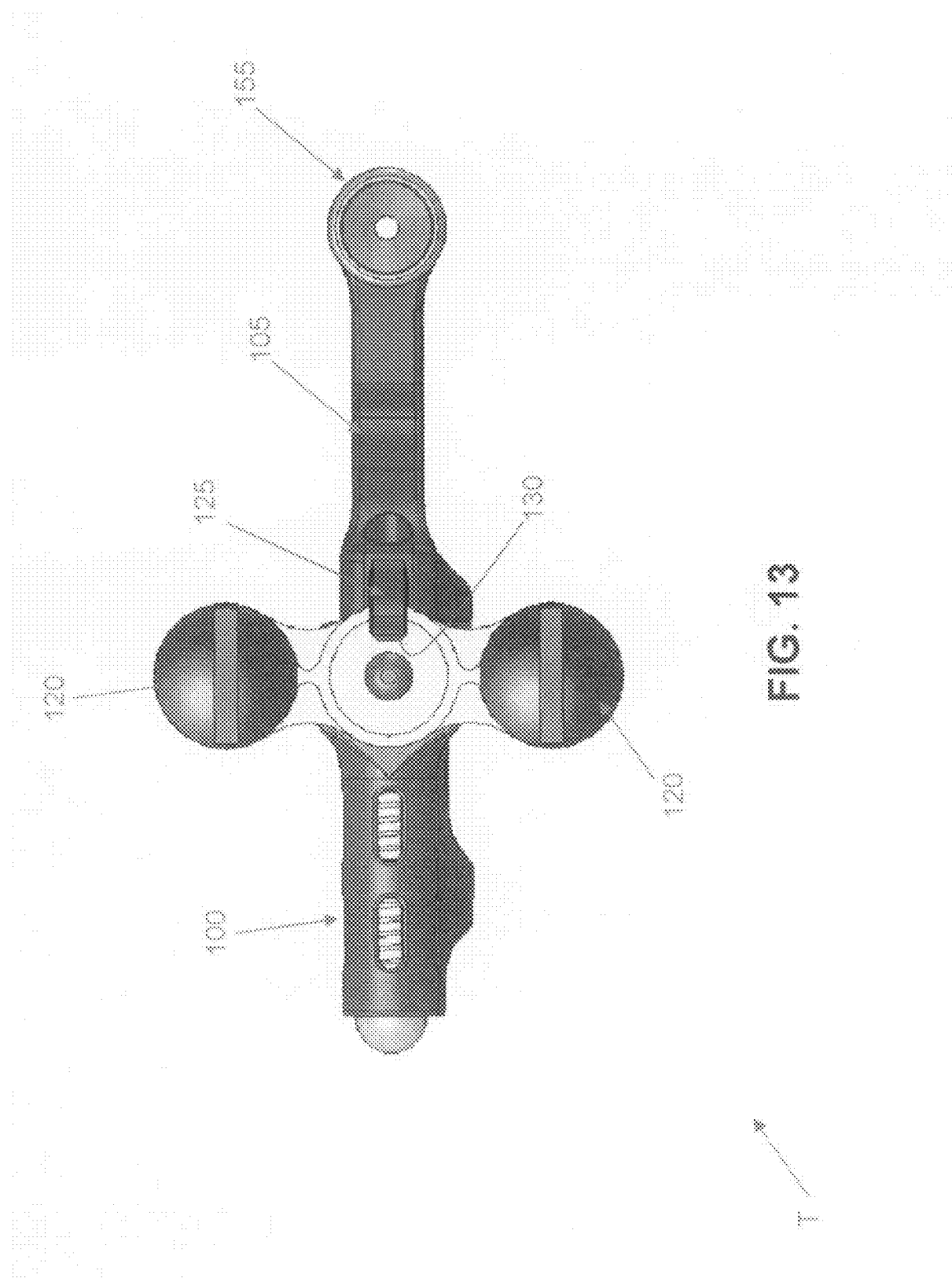
Figure 27:
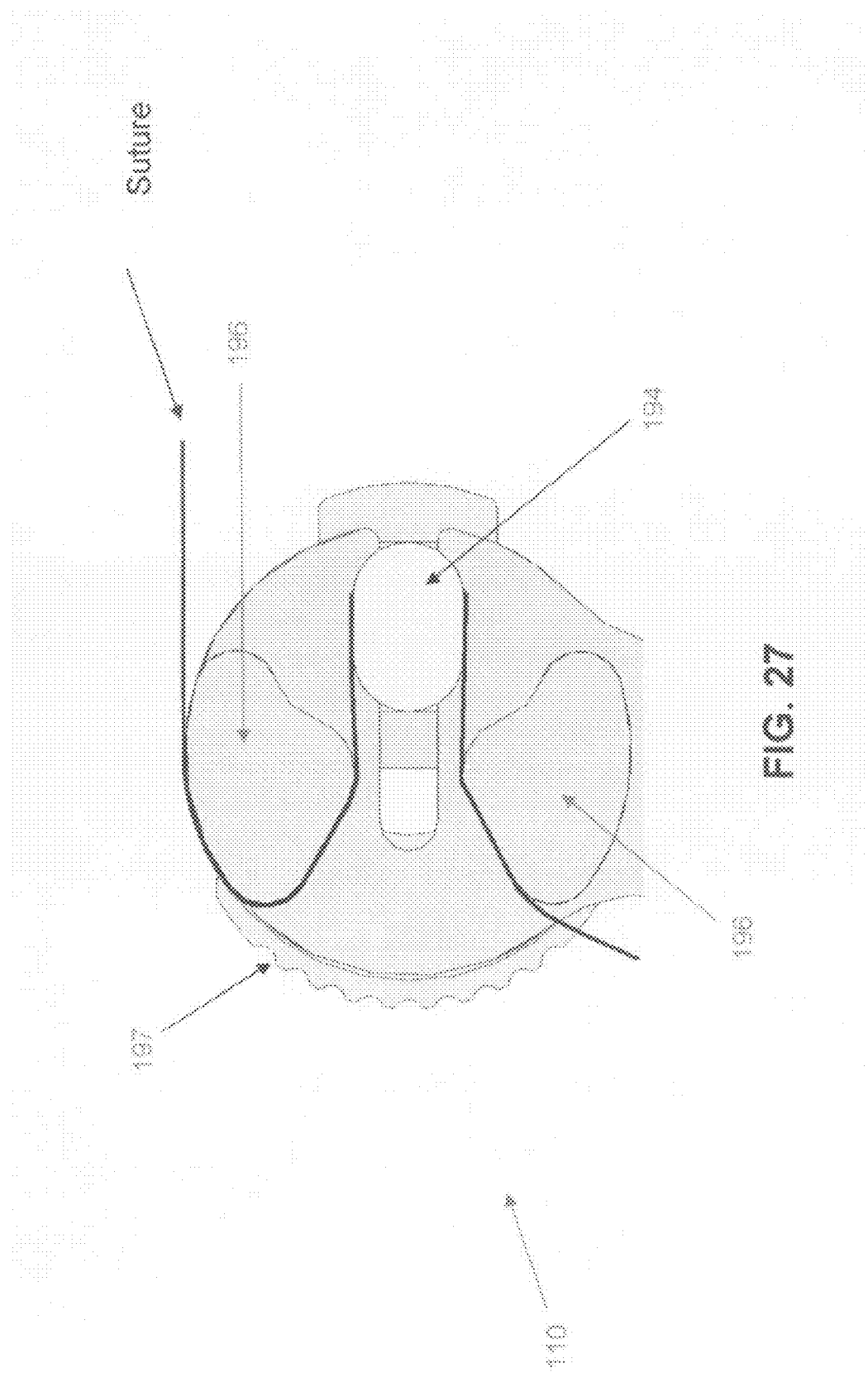

Looking now at FIGS. 12-17, in another preferred embodiment of the present invention, tensioner T may comprise a two-part slide body (i.e., a distal body 100 and a proximal body 105, spring biased together as will hereinafter be discussed), with a set of suture cleat assemblies 110 attached to distal body 100. Again, tensioner T may be used with four-strand ligament reconstructions, two-strand ligament reconstructions, etc. Each suture cleat assembly 110 attaches to lateral pivot fingers 115 located on distal body 100. Each suture cleat assembly 110 has two cleats 120 on opposing ends of the cleat assembly. Suture cleat assemblies 110 can be locked into a vertical position when not under tension, i.e., by virtue of the engagement of proximal body fingers 125 with cleat assembly grooves 130 (FIG. 13).

Distal body 100 is attached to proximal body 105 by rails 135 extending through bores 140 in distal body 100. Compression springs 145 are captured on the rails within bores 140 of distal body 100. More particularly, springs 145 are captured on rails 135 between the enlarged heads 147 of rails 135 and the bases of bores 140. The proximal ends of the rails extend through openings in the distal body and are secured to proximal body 105. Distal body 100 has windows 150 to provide the surgeon with a visual gauge of the degree of tension being applied to the graft ligament strands during use.

Proximal body 105 has a handle 155 attached to it so as to enable one-handed operation of tensioner T.

In use, suture strands (e.g., four or two strands) can be looped and/or wound around cleats 120 so as to secure the suture strands to the cleats. Preferably, one suture strand is attached to each cleat. Where tensioner T is used in a four-strand reconstruction, all four of the cleats 120 are used to secure separate suture strands; where tensioner T is used in a two-strand reconstruction, two of the cleats are used to secure separate suture strands and two of the cleats are let unused. After the suture strands are attached to the cleats, the surgeon pulls the handle proximally, away from the patient, so as to tension the graft ligament strands to the desired tension. The graft ligament strands can then be fixed in place by any of the several fixation techniques well known to those skilled in the art.

Significantly, inasmuch as cleat assemblies 110 are each independently mounted (e.g., via pivot fingers 115) to distal body 100, the cleat assemblies 110 can rotate independently of one another. As a result, tensioner T can more easily balance the tension applied to each ligament strand.

Cleat Assemblies

It should be appreciated that the suture cleat assemblies 110 used with novel tensioner T shown in FIGS. 12-17 may comprise any of a variety of different constructions and components.

Looking next at FIGS. 18-21, suture cleat assembly 110 may comprise an inner cleat 160 and an outer cleat 165. Inner cleat 160 is seated within a recess 170, mounted on a spring 175, so that the inner cleat 160 is biased outboard of the cleat assembly body 180. Inner cleat 160 and recess 170 have non-circular shapes in order to lock inner cleat 160 against rotation when inner cleat 160 is seated within recess 170. Outer cleat 165 has a stem 185 which extends through inner cleat 160 and mounts to cleat assembly body 180. When a suture strand is wound around stem 185, spring 175 compresses and allows the suture strand to be captured between inner cleat 160 and outer cleat 165.

In an alternate embodiment, and looking now at FIGS. 22-25, suture cleat assembly 110 may comprise an inner cleat 186 and an outer cleat 187. Inner cleat 186 is mounted on an axle 188, over a spring 189, so that inner cleat 186 is biased outboard of the cleat assembly body 190. Inner cleat 186 has a slot 191 which mates around the base 192 of cleat assembly body 190 to lock inner cleat 186 against rotation about axle 188. Outer cleat 187 has a stem 193 which extends through inner cleat 186 and mounts on axle 188. When a suture strand is wound around stem 193, spring 189 compresses and allows the suture strand to be captured between inner cleat 186 and outer cleat 187.

Figure 28:
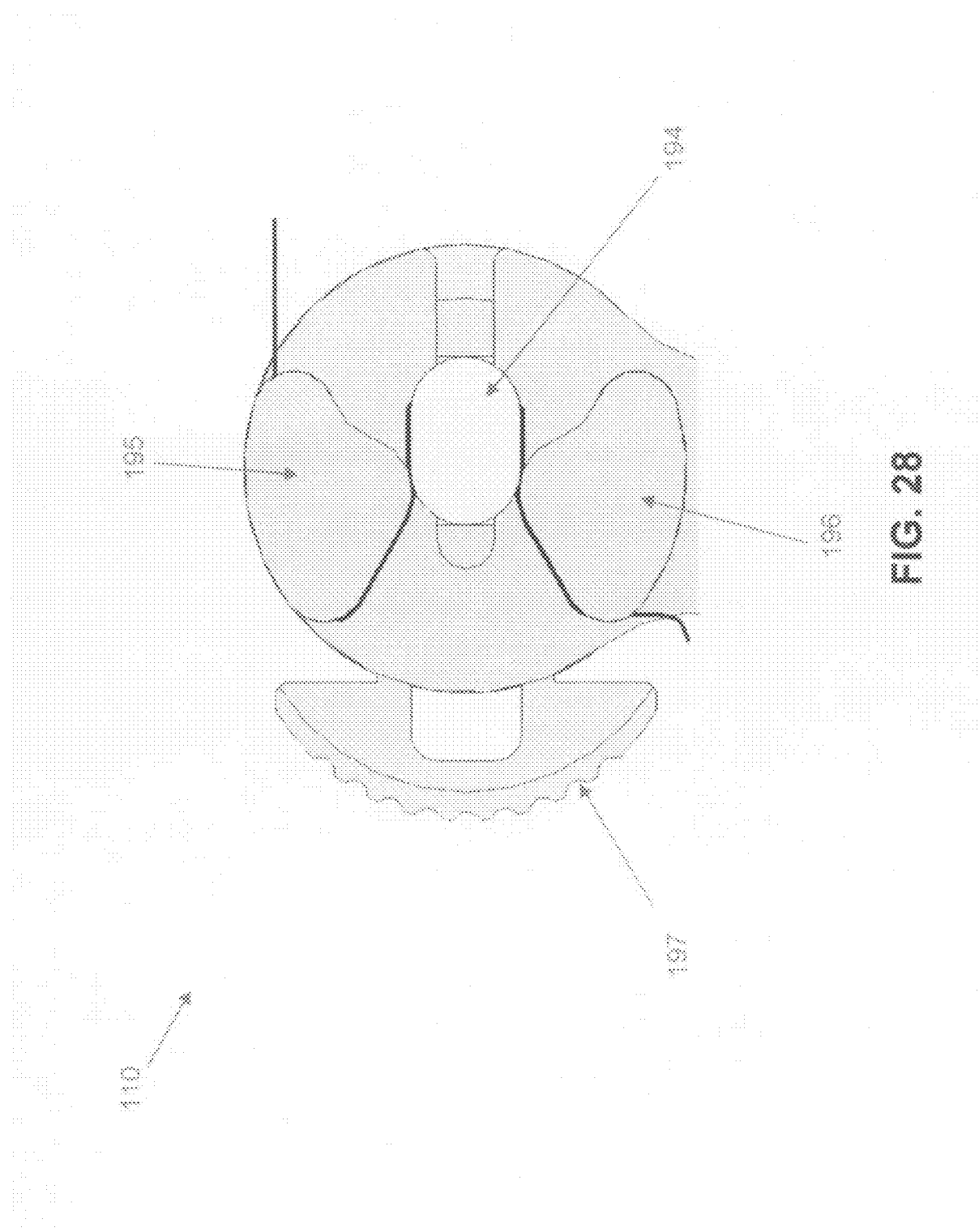
Figure 29:
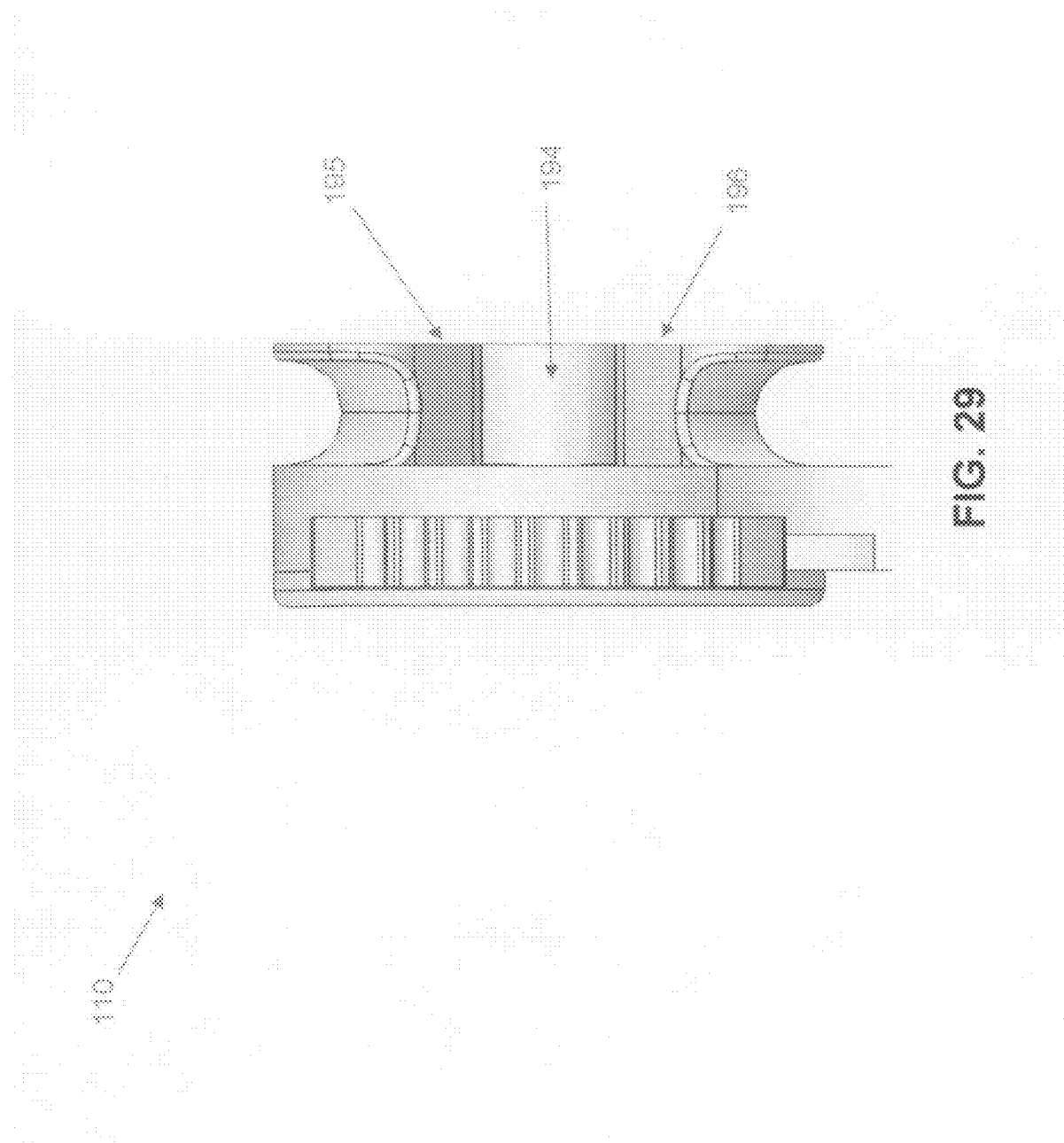

FIGS. 26-29 show another cleat assembly 110. With this construction, a slide 194 on the cleat may be moved between an open position (FIG. 27) and a closed position (FIG. 28). More particularly, slide 194 is set in its open position (FIG. 27) and suture is wound around the upper mandrel 195, slide 194, and the lower mandrel 196. Then slide 194 is moved to its closed position (FIG. 28) so as to capture the suture between the upper and lower mandrels 195, 196 and slide 194. When the suture is to be released, slide 194 is moved back to its open position (FIG. 27) and the suture withdrawn from the upper and lower mandrels 195, 196 and slide 194. A button 197 is used to move slide 194 between its open and closed positions.

Third Preferred Embodiment of the Novel Tensioner

Figure 30:
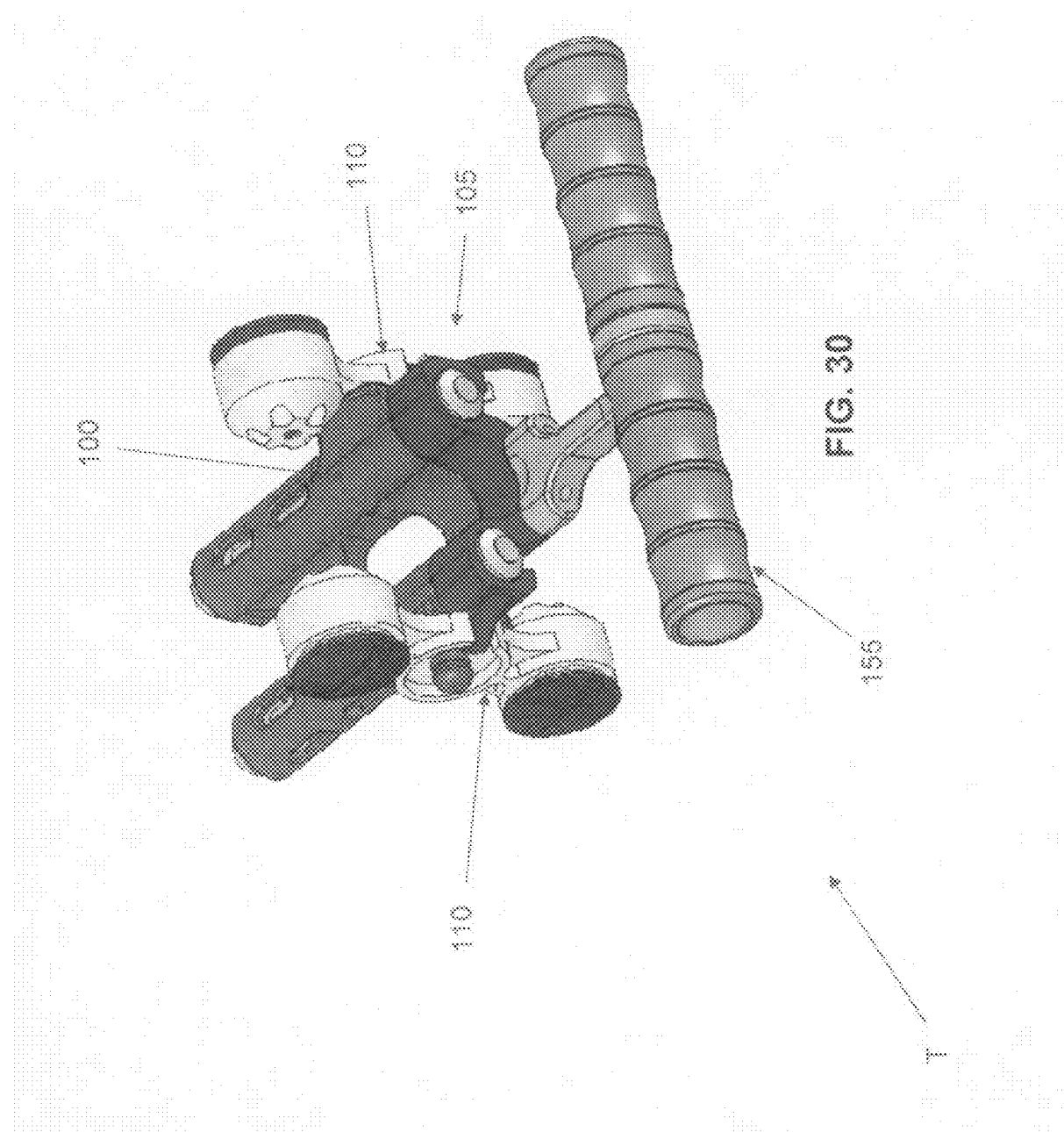
FIGS. 30-32 show a third preferred embodiment of the novel graft ligament strand tensioner of the present invention.
Figure 31:
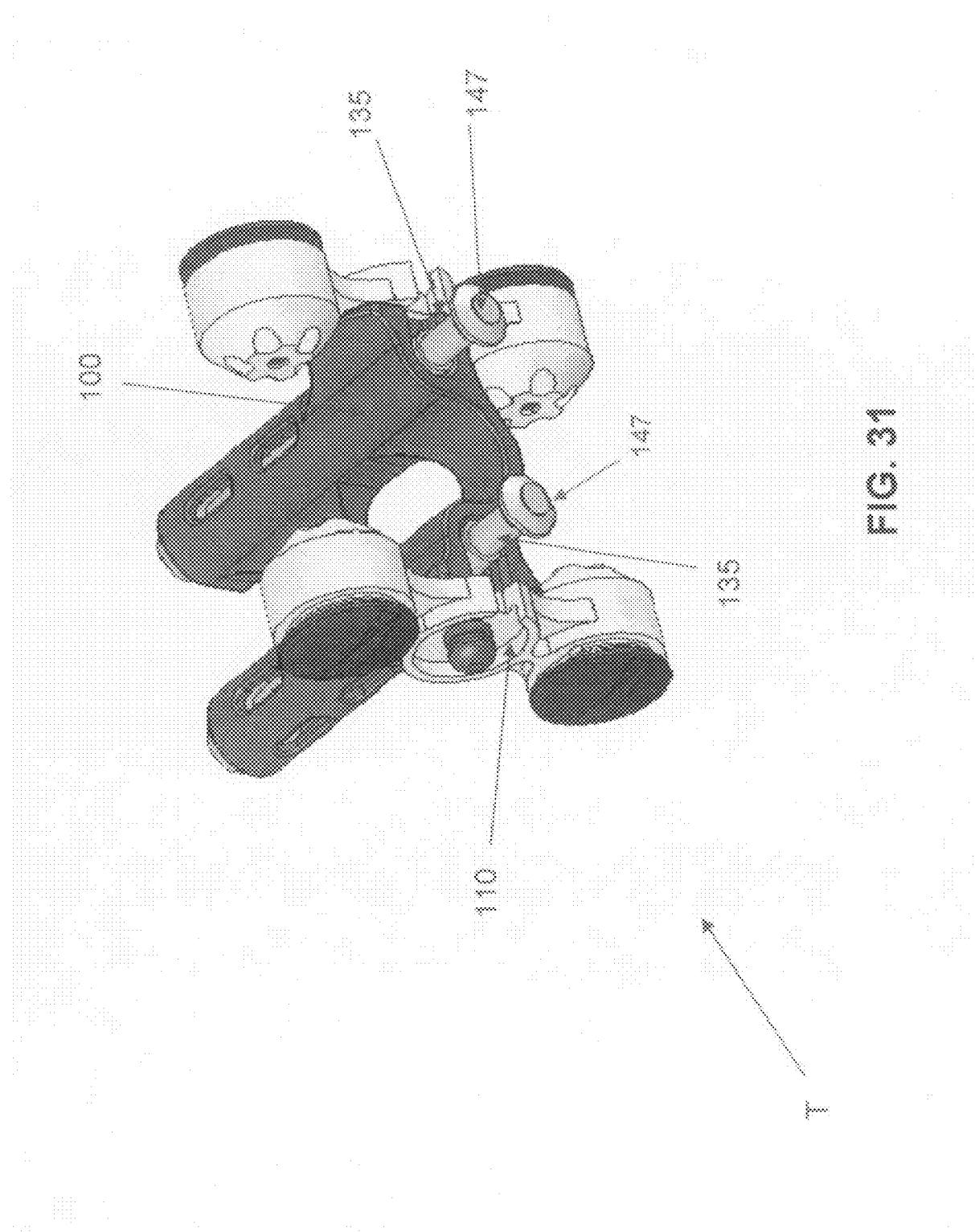
Figure 32:
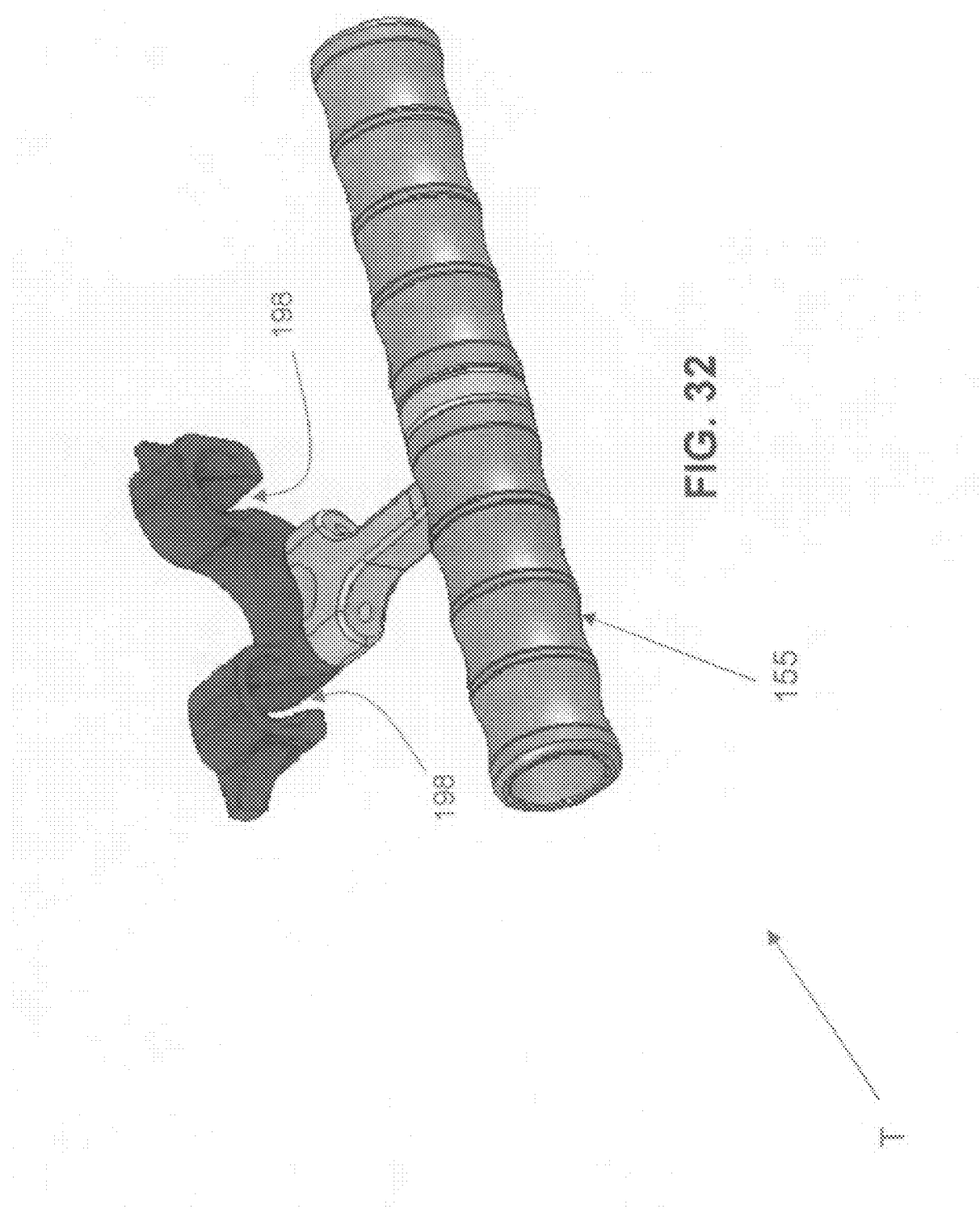
Figure 33:
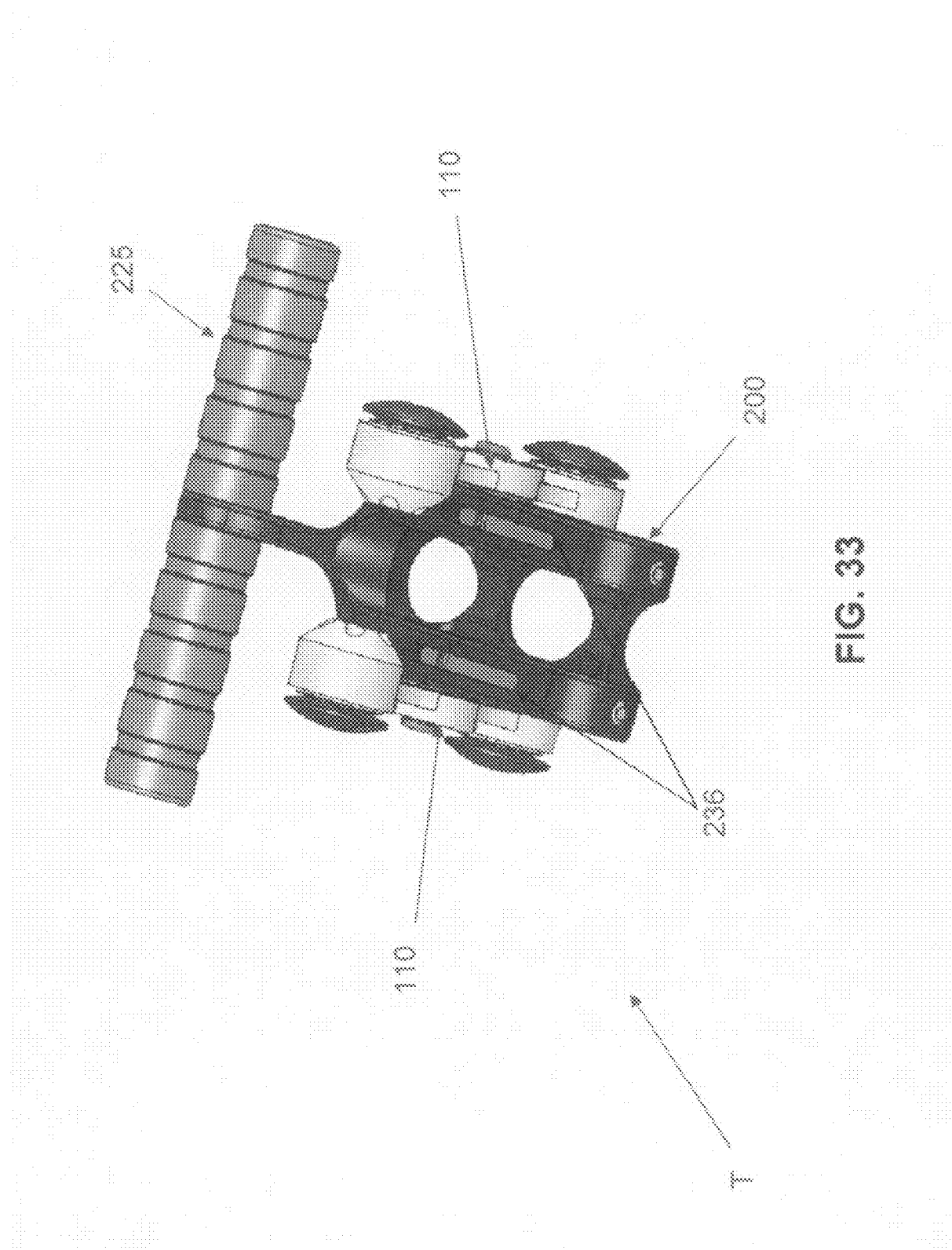
FIGS. 33-36 show a fourth preferred embodiment of the novel graft ligament strand tensioner of the present invention.
Figure 34:
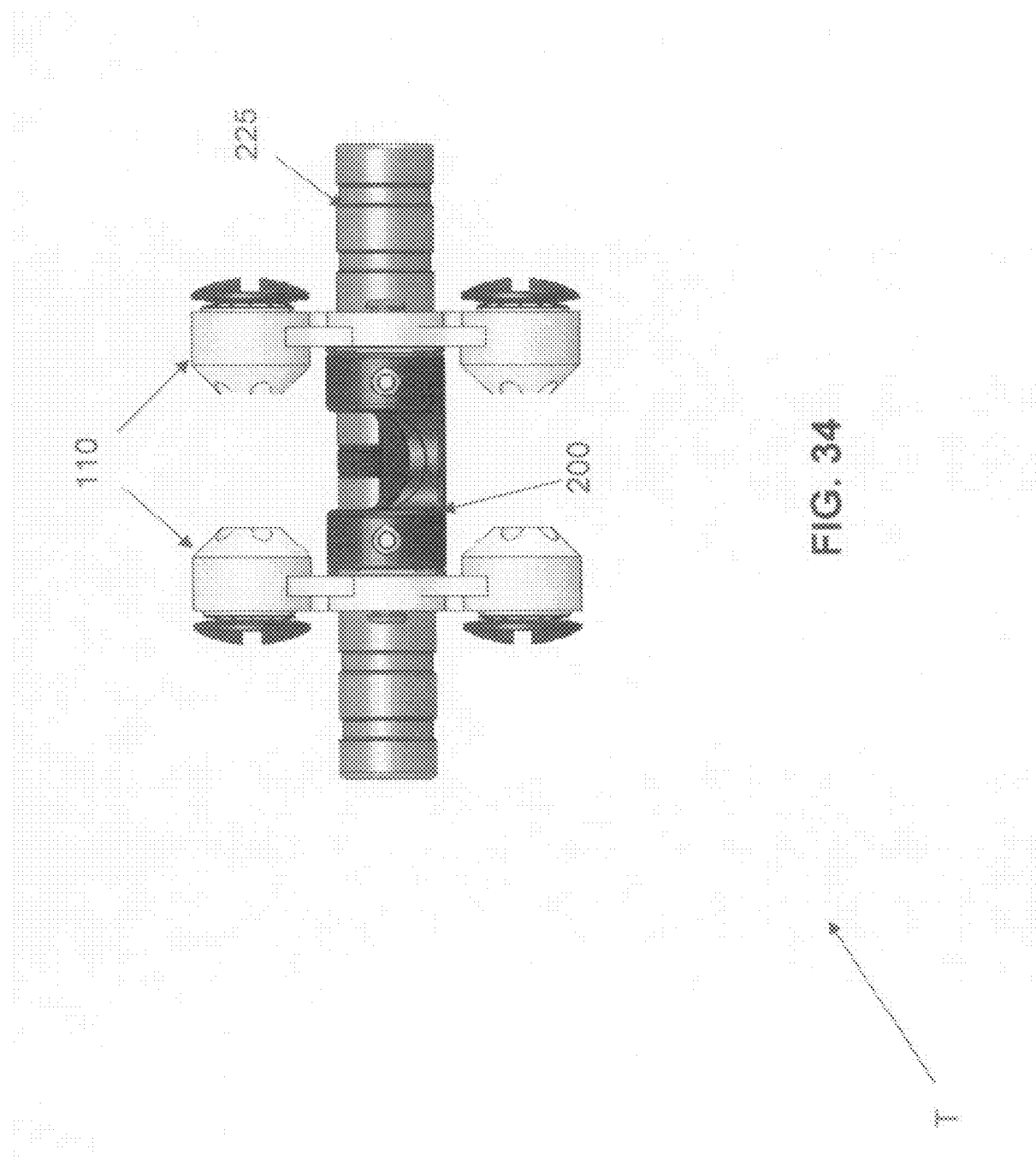

Looking next at FIGS. 30-32, another preferred embodiment of the present invention is shown. The novel tensioner T is generally similar to the tensioner T shown in FIGS. 12-17, except that with the construction shown in FIGS. 30-32, proximal body 105 has grooves 198 for capturing enlarged ends 147 of slide rails 135 as slide rails 135 extend from the bore within distal body 100. As a result of this construction, proximal body 105 can be attached to distal body 100 during use, but proximal body 105 can be easily disconnected from distal body 100, e.g., for cleaning and storage.

Fourth Preferred Embodiment of the Novel Tensioner

In another preferred embodiment of the present invention, and looking next at FIGS. 33-36, tensioner T may comprise a body 200 with internal rails 205, springs 210 mounted on rails 205, sliders 215 slidably mounted on rails 205, and suture cleat assemblies 110 mounted to sliders 215. More particularly, rails 205 are disposed within bores 220 in body 200. Springs 210 and sliders 215 are mounted on rails 205, with springs 210 biasing sliders 215 proximally (i.e., toward handle 225). Sliders 215 comprise fingers 230 which extend through openings 235 formed in the sidewalls of body 200; suture cleat assemblies 110 are mounted to fingers 230, so that suture cleat assemblies 110 move with sliders 215. Force view windows 236 are provided so as to provide the surgeon with visual feedback with respect to the amount of tension being applied. Handle 225 is secured to body 200 so as to enable one-handed operation of tensioner T.

In use, suture strands (e.g., four or two strands) are looped and/or wound around cleats 120. After the suture strands are attached to cleats 120, the surgeon pulls handle 225 proximally and the graft ligament strands are tensioned to the desired degree. The graft strands can then be fixed in place by any of the several fixation techniques well known to those skilled in the art.

Figure 35:
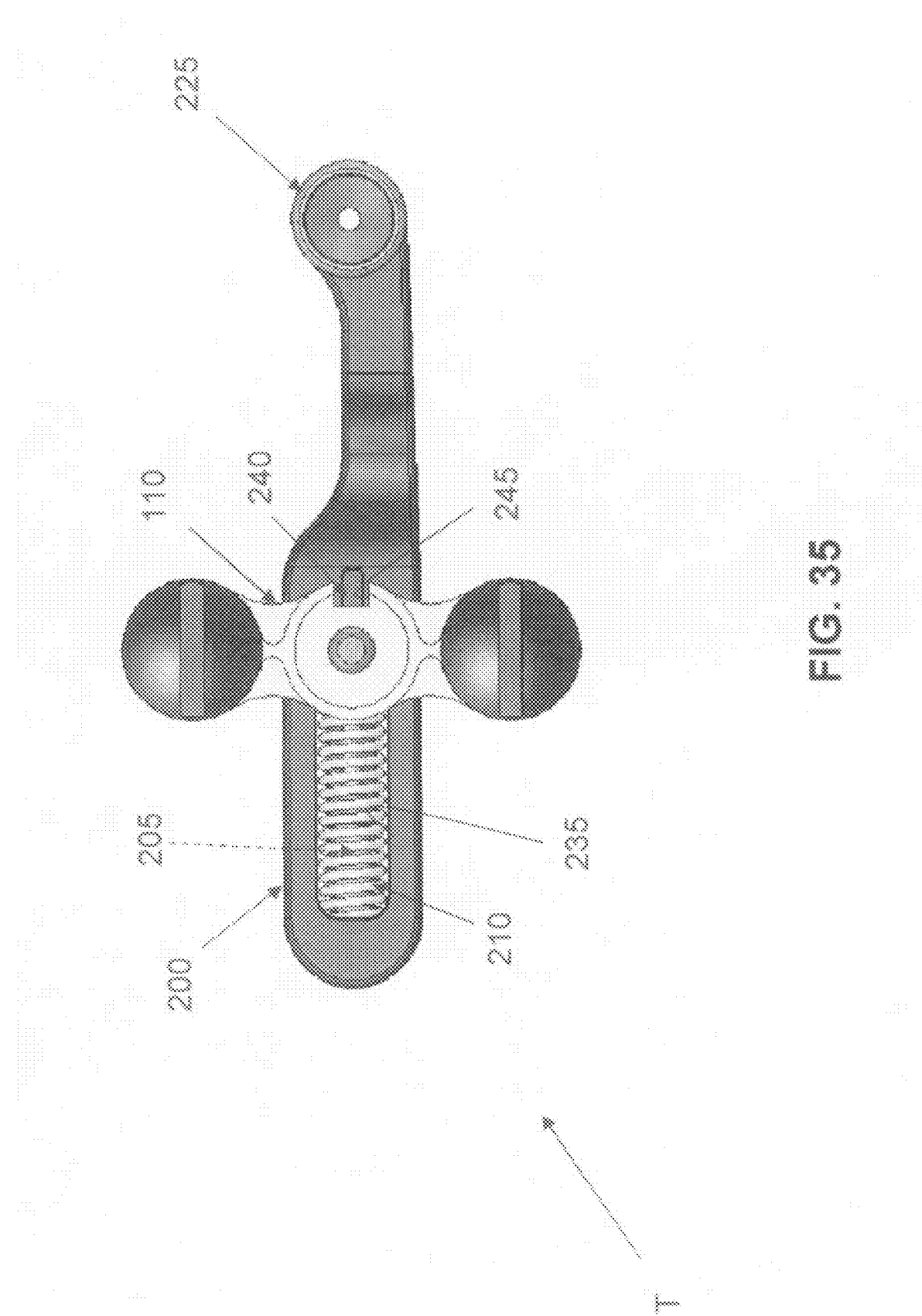
Figure 36:
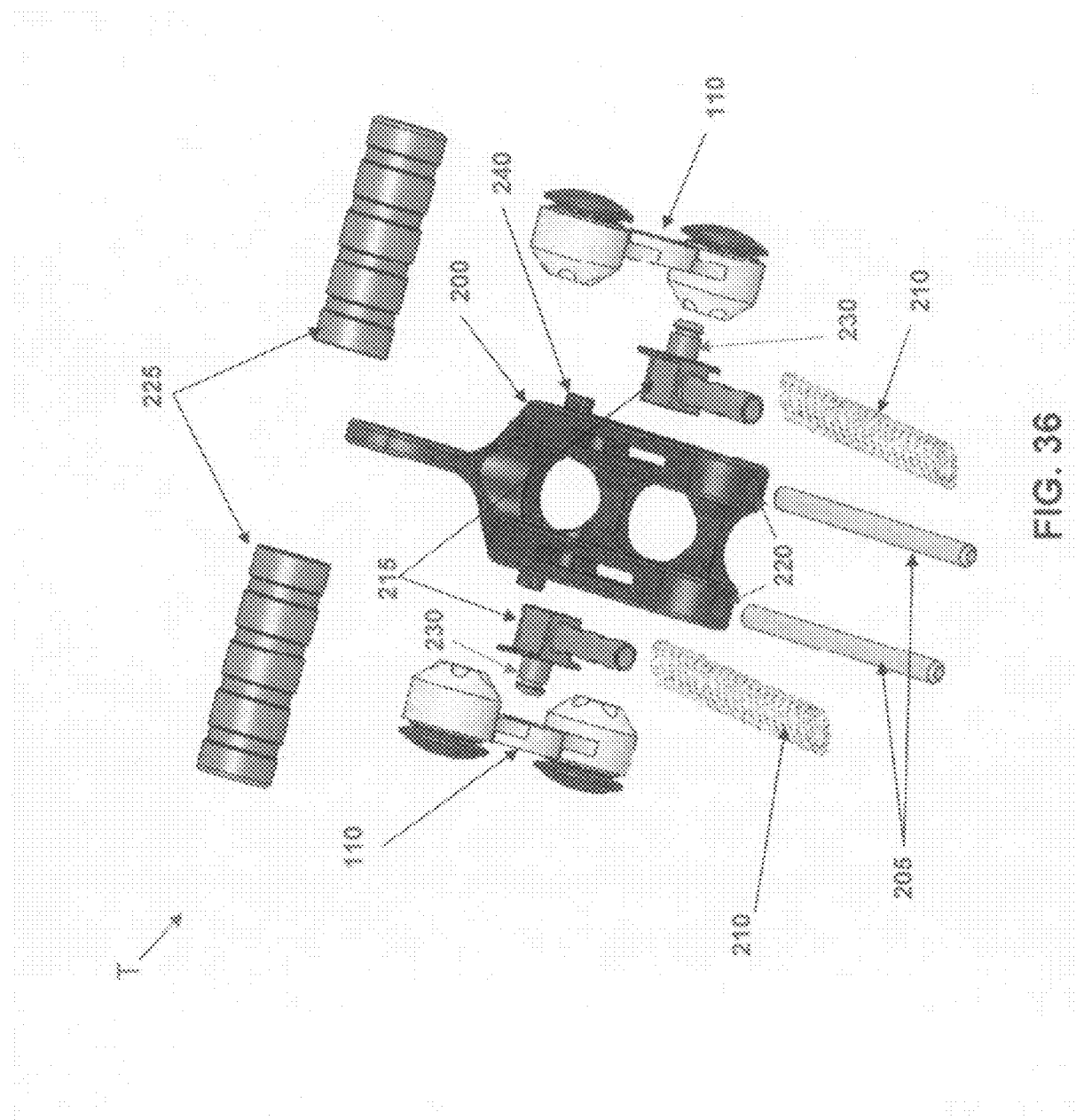

Body 200 may include an anti-rotation boss 240, and cleat assembly 110 may include an anti-rotation groove 245, so that cleat assemblies 110 may be stabilized in the position shown in FIG. 35 when tensioner T is not under tension.

Significantly, inasmuch as cleat assemblies 110 are each independently mounted (e.g., via sliders 215 and rails 205) to body 200, the cleat assemblies 110 can move longitudinally independently of one another. As a result, tensioner T can more easily balance the tension applied to each ligament strand.

Fifth Preferred Embodiment of the Novel Tensioner

Figure 37:
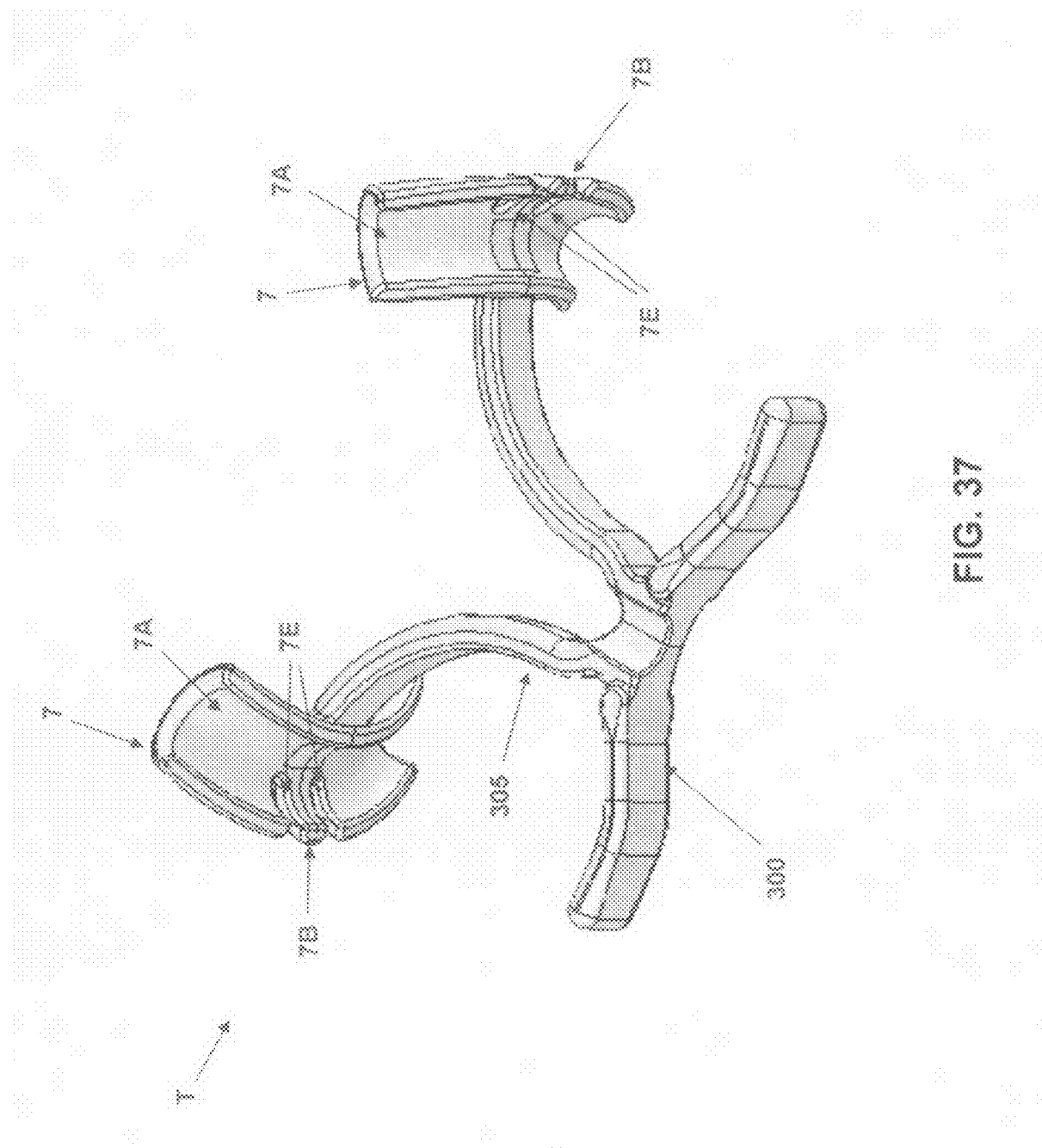
FIG. 37 shows a fifth preferred embodiment of the novel graft ligament strand tensioner of the present invention.

In another embodiment of the present invention, and looking next at FIG. 37, tensioner T may comprise a "unibody" design. In this construction, tensioner T has a handle 300 which is "rigidly" connected via a body 305 to two suture rails 7, i.e., there is no spring assembly intervening between the handle and the two suture rails. Suture rails 7 preferably include grooved outer channels 7A and central mandrels 7B, whereby to facilitate a four-strand graft ligament reconstruction and a two-strand graft ligament reconstruction, respectively. Preferably, central mandrels 7B are formed by providing a pair of slots 7E in each of the grooved outer channels 7A.

Sixth Preferred Embodiment of the Novel Tensioner

Figure 38:
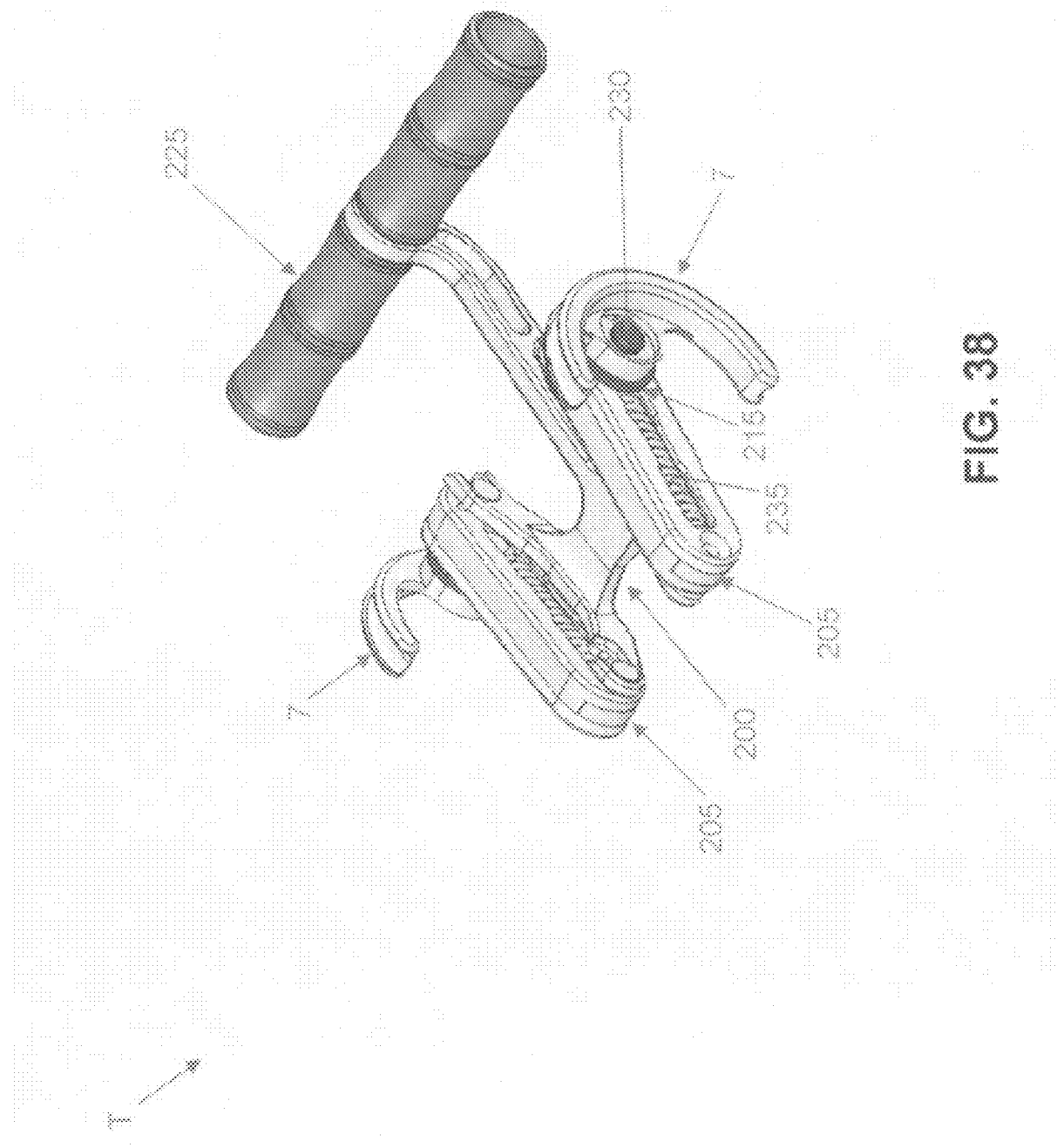
FIGS. 38-40 show a sixth preferred embodiment of the novel graft ligament strand tensioner of the present invention.
Figure 39:
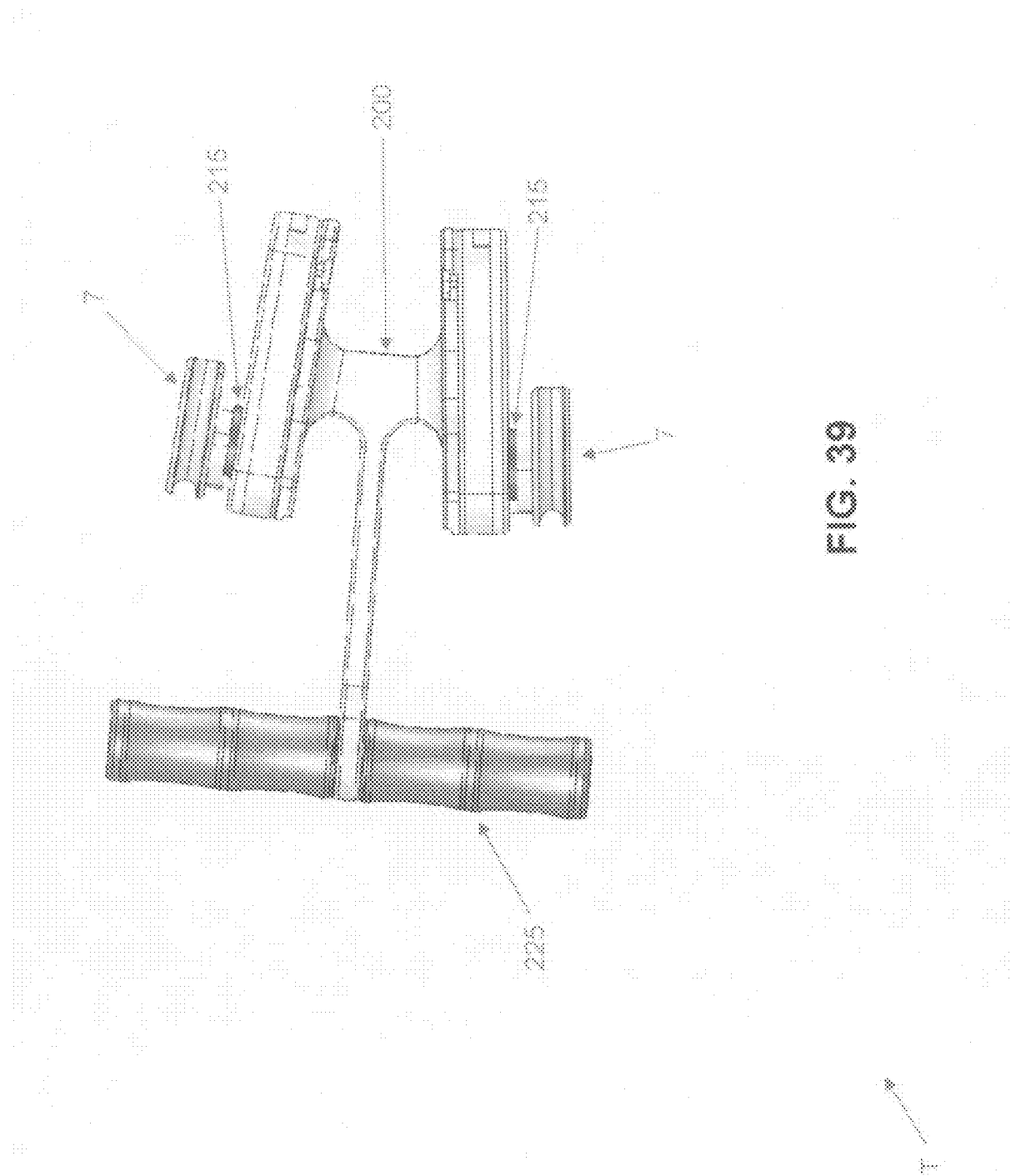
Figure 40:
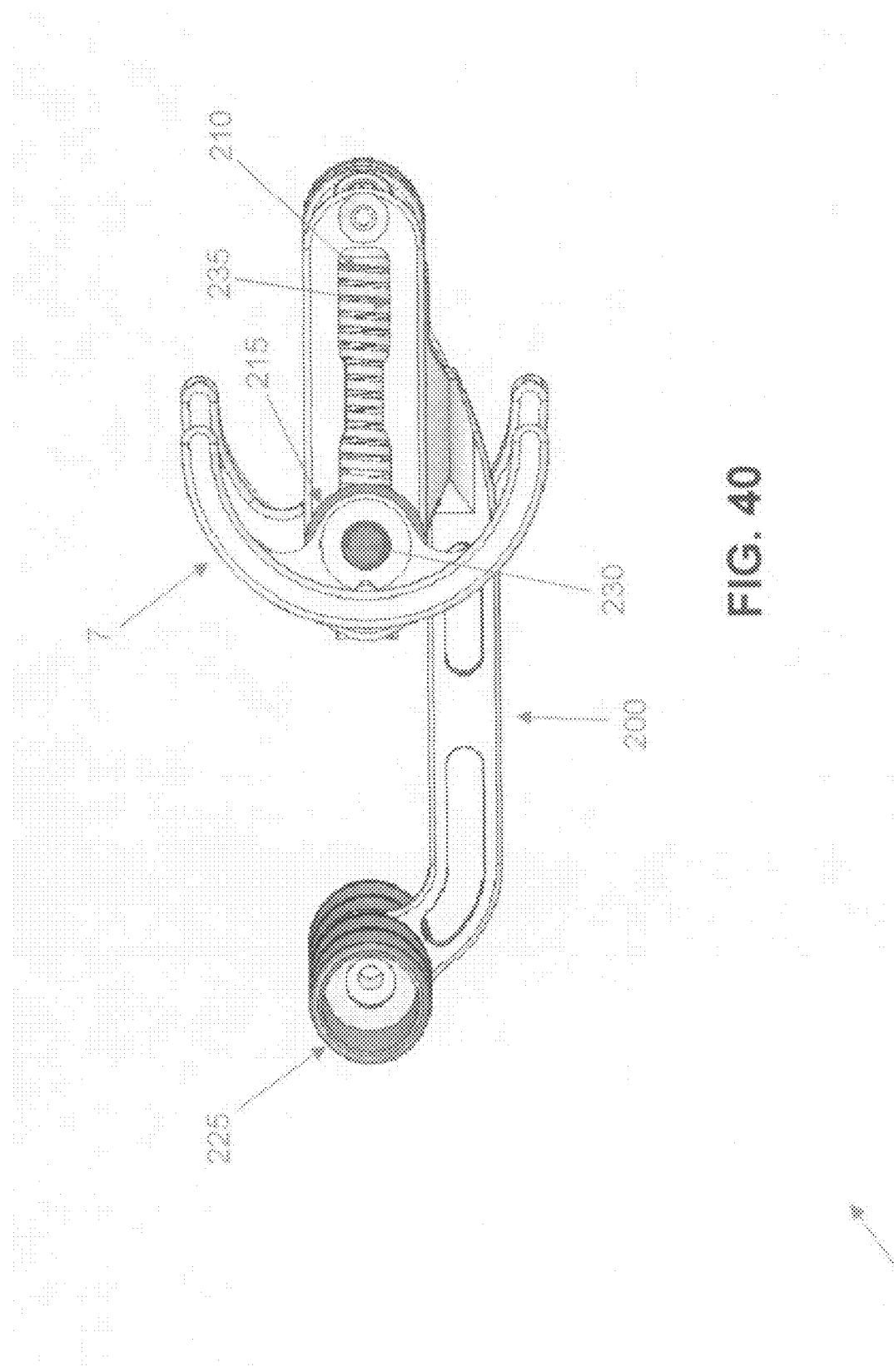

Another preferred construction is shown in FIGS. 38-40. More particularly, in FIGS. 38-40 there is shown a tensioner T which is generally similar to the tensioner T shown in FIGS. 33-36, except that (i) the body 200 shown in FIGS. 38-40 has a different geometry than the body 200 shown in FIGS. 33-36, and (ii) suture cleat assemblies 110 are replaced by suture rails 7.

Modifications of the Preferred Embodiments

It should be understood that many additional changes in the details, operation, steps and arrangements of elements, which have been herein described and illustrated in order to explain the nature of the present invention, may be made by those skilled in the art while still remaining within the principles and scope of the invention.

What is claimed is:

1. A graft ligament strand tensioner comprising:
a body; and
a pair of suture rails connected to the body, wherein each suture rail comprises a grooved outer channel for receiving a suture loop and a central mandrel for receiving a suture loop, wherein the suture rails are selectively rotatably mounted to the body such that (i) the suture rails are free to rotate when tension is applied to the suture rails, and (ii) the suture rails are locked against rotation when tension is not applied to the suture rails.

2. A graft ligament strand tensioner comprising:
a body defining a longitudinal axis,
a pair of suture rails connected to the body for releasably engaging a pair of sutures, the pair of suture rails being connected to the body, in spaced-apart fashion, symmetrically about a center axis of the body, wherein the suture rails are selectively rotatably mounted to the body such that (i) the suture rails are free to rotate when tension is applied to the suture rails, and (ii) the suture rails are locked against rotation when tension is not applied to the suture rails; and
a handle pivotally connected to the body such that the handle can be pivoted relative to the longitudinal axis of the body only when the handle is under tension.

3. A graft ligament strand tensioner according to claim 2 wherein each suture rail comprises a grooved outer channel for receiving a suture loop and a central mandrel for receiving a suture loop, wherein the separation of a suture loop received by the grooved outer channel is larger than the separation of a suture loop received by the central mandrel.

4. A graft ligament strand tensioner according to claim 2 wherein the pair of suture rails are disposed in spaced-apart fashion symmetrically about a center axis of the body.

* * * * *